US012577543B2

(12) United States Patent
Yamaguchi et al.

(10) Patent No.: US 12,577,543 B2
(45) Date of Patent: Mar. 17, 2026

(54) METHOD FOR PRODUCING POLYISOPRENOID BY REACTION CATALYZED BY MUTANT CIS-PRENYLTRANSFERASE (CPT) FAMILY PROTEIN, AND METHOD FOR PRODUCING RUBBER PRODUCT

(71) Applicants: SUMITOMO RUBBER INDUSTRIES, LTD., Kobe (JP); TOHOKU UNIVERSITY, Sendai (JP); KANAZAWA UNIVERSITY, Kanazawa (JP); NATIONAL UNIVERSITY CORPORATION SAITAMA UNIVERSITY, Saitama City (JP)

(72) Inventors: Haruhiko Yamaguchi, Kobe (JP); Yukino Inoue, Kobe (JP); Seiji Takahashi, Sendai (JP); Toru Nakayama, Sendai (JP); Satoshi Yamashita, Kanazawa (JP); Yuzuru Tozawa, Saitama (JP)

(73) Assignees: SUMITOMO RUBBER INDUSTRIES, LTD., Kobe (JP); TOHOKU UNIVERSITY, Sendai (JP); KANAZAWA UNIVERSITY, Kanazawa (JP); NATIONAL UNIVERSITY CORPORATION SAITAMA UNIVERSITY, Saitama City (JP)

( * ) Notice: Subject to any disclaimer, the term of this patent is extended or adjusted under 35 U.S.C. 154(b) by 139 days.

(21) Appl. No.: 18/165,191

(22) Filed: Feb. 6, 2023

(65) Prior Publication Data

US 2023/0279371 A1 Sep. 7, 2023

(30) Foreign Application Priority Data

Mar. 2, 2022 (JP) ................................. 2022-031813

(51) Int. Cl.
| | |
|---|---|
| *C12P 5/00* | (2006.01) |
| *B60C 1/00* | (2006.01) |
| *C12N 9/10* | (2006.01) |
| *C12N 15/82* | (2006.01) |

(52) U.S. Cl.
CPC .......... *C12N 9/1085* (2013.01); *B60C 1/0041* (2013.01); *C12N 15/8257* (2013.01); *C12P 5/007* (2013.01); *C12Y 205/0102* (2013.01)

(58) Field of Classification Search
CPC .............. C12N 9/1085; C12N 15/8257; C12N 15/8243; B60C 1/0041; C12P 5/007; C12Y 205/0102; C07K 2319/00
See application file for complete search history.

(56) References Cited

U.S. PATENT DOCUMENTS

| | | | |
|---|---|---|---|
| 9,127,286 | B2 | 9/2015 | Nakazawa et al. |
| 10,000,774 | B2 | 6/2018 | Yamaguchi |
| 10,385,362 | B2 | 8/2019 | Inoue et al. |
| 10,907,179 | B2 * | 2/2021 | Yamaguchi .......... C07K 14/415 |
| 11,236,365 | B2 | 2/2022 | Inoue et al. |
| 2003/0236208 | A1 | 12/2003 | Kmiec et al. |
| 2004/0078840 | A1 | 4/2004 | Chappell et al. |
| 2007/0199099 | A1 | 8/2007 | Hallahan et al. |
| 2009/0288226 | A1 | 11/2009 | Hallahan et al. |
| 2010/0218272 | A1 | 8/2010 | Nakazawa et al. |
| 2011/0201771 | A1 | 8/2011 | Puskas et al. |
| 2015/0266988 | A1 | 9/2015 | Kojima et al. |
| 2015/0322446 | A1 | 11/2015 | Yamaguchi et al. |
| 2016/0244773 | A1 | 8/2016 | Inoue et al. |
| 2016/0244775 | A1 | 8/2016 | Inoue et al. |
| 2016/0244776 | A1 | 8/2016 | Inoue et al. |
| 2017/0051313 | A1 | 2/2017 | Inoue et al. |
| 2018/0171364 | A1 | 6/2018 | Yamaguchi et al. |
| 2019/0323039 | A1 | 10/2019 | Inoue et al. |
| 2019/0376093 | A1 | 12/2019 | Sakurai et al. |
| 2021/0292797 | A1 | 9/2021 | Lee et al. |
| 2023/0167465 | A1 | 6/2023 | Yamaguchi et al. |

FOREIGN PATENT DOCUMENTS

| | | |
|---|---|---|
| CN | 104684987 A | 6/2015 |
| CN | 113388594 A | 9/2021 |
| CN | 113480660 A | 10/2021 |
| EP | 3 097 775 A1 | 11/2016 |
| EP | 3 309 257 A1 | 4/2018 |
| JP | 2003-18999 A | 1/2003 |

(Continued)

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Lin et al., National Science Review 5:78-87, 2018.*
Lazar et al., "Transforming Growth Factor α: an Aromatic Side Chain at Position 38 Is Essential for Biological Activity," Molecular and Cellular Biology, vol. 9, No. 2, Feb. 1989, pp. 860-864.

(Continued)

*Primary Examiner* — Delia M Ramirez
(74) *Attorney, Agent, or Firm* — Birch, Stewart, Kolasch & Birch, LLP

(57) ABSTRACT

Provided are a mutant cis-prenyltransferase (CPT) family protein and a method for producing a polyisoprenoid, which enable the production of a high molecular weight polyisoprenoid. Included is a mutant cis-prenyltransferase (CPT) family protein obtained by mutating the amino acid sequence of a C-terminal region of a cis-prenyltransferase (CPT) family protein not found on rubber particles to be identical or similar to the amino acid sequence of a C-terminal region of a cis-prenyltransferase (CPT) family protein found on rubber particles.

7 Claims, 4 Drawing Sheets

Specification includes a Sequence Listing.

(56)                References Cited

FOREIGN PATENT DOCUMENTS

| JP | 2003-310295 A | 11/2003 |
| JP | 2005-500840 A | 1/2005 |
| JP | 2005-225796 A | 8/2005 |
| JP | 2005-308412 A | 11/2005 |
| JP | 2005-312436 A | 11/2005 |
| JP | 2009-221306 A | 10/2009 |
| JP | 2010-119373 A | 6/2010 |
| JP | 2010-132594 A | 6/2010 |
| JP | 2011-52146 A | 3/2011 |
| JP | 2011-188776 A | 9/2011 |
| JP | 5035871 B2 | 9/2012 |
| JP | 2014-11972 A | 1/2014 |
| JP | 5383197 B2 | 1/2014 |
| JP | 2014-227487 A | 12/2014 |
| JP | 2015-136296 A | 7/2015 |
| JP | 2016-93186 A | 5/2016 |
| JP | 2016-149973 A | 8/2016 |
| JP | 2016-154458 A | 9/2016 |
| WO | WO 03/010294 A2 | 2/2003 |
| WO | WO 2004/044173 A2 | 5/2004 |
| WO | WO 2004/106531 A1 | 12/2004 |
| WO | WO 2012/152923 A1 | 11/2012 |
| WO | WO 2018/116726 A1 | 6/2018 |

OTHER PUBLICATIONS

"Hevea brasiliensis HRT1 mRNA for cis-prenyltransferase, complete cds," GenBank, Accession No. AB061234, Retreived Online: ncbi.nlm.nih.gov/nuccore/1519311382, Nov. 22, 2018, 2 pages total.

"Taraxacum kok-saghyz cis-crenyl transferase 1 (CPT1) mRNA, partial cds," GenBank, Accession No. KT899437, Retreived Online: ncbi.nlm.nih.gov/nuccore/KT899437, Feb. 2, 2016, 1 page total.

Amerik et al., "Regulation of Natural Rubber Biosynthesis by Proteins Associated with Rubber Particles," Russian Journal of Bioorganic Chemistry, vol. 44, No. 2, 2018, pp. 140-149.

Bae et al., "Lipid Composition of Latex and Rubber Particles in Hevea brasiliensis and Taraxacum kok-saghyz," Molecules, vol. 25, 5110, 2020, pp. 1-13.

Grabinska et al., "cis-Prenyltransferase: New Insights into Protein Glycosylation, Rubber Synthesis, and Human Diseases," The Journal of Biological Chemistry, vol. 291, No. 35, Aug. 26, 2016, pp. 18582-18590.

Liang et al., "Structure, mechanism and function of prenyltransferases," European Journal of Biochemistry, vol. 269, 2002, pp. 3339-3354.

Aoki et al., "Identification of Laticifer-specific Genes and their Promoter Regions from a Natural Rubber Producing Plant Hevea brasiliensis," Plant Science, vol. 225, 2014 (Available online May 12, 2014), pp. 1-8.

Asawatreratanakul et al., "Molecular Cloning, Expression and Characterization of cDNA Encoding cis-prenyltransferases from Hevea brasiliensis," Eur. J. Biochem., vol. 270, 2003, pp. 4671-4680.

Bennett, "Sunflowers Make Rubber a Reality," https://www.agweb.com/news/crops/sunflowers-make-rubber-reality (2017), pp. 1-4.

Berthelot et al., "Hevea brasiliensis REF (Hev b 1) and SRPP (Hev b 3): an Overview on Rubber Particle Proteins," Biochimie, vol. 106, 2014 (Available online Jul. 11, 2014), pp. 1-9.

Branden et al., "Introduction to Protein Structure," Garland Publishing Inc., New York, 1991, p. 247 (3 pages total).

Brasher et al., "A Two-component Enzyme Complex is Required for Dolichol Biosynthesis in Tomato," The Plant Journal, vol. 82, 2015 (published online Apr. 21, 2015), pp. 903-914.

Dai et al., "In-depth proteome analysis of the rubber particle of Hevea brasiliensis (para rubber tree)," Plant Molecular Biology, vol. 82, 2013 (published online Apr. 4, 2013), pp. 155-168.

Epping et al., "A rubber transferase activator is necessary for natural rubber biosynthesis in dandelion," Nature Plants, vol. 1, Article No. 15048, May 2015 (published Apr. 27, 2015), XP055372960, pp. 1-9.

Friedberg, "Automated protein function prediction-the genomic challenge," Briefings in Bioinformatics, vol. 7, No. 3, 2006, pp. 225-242.

Goodman, "Polymer biosynthesis: Rubber ramps up," Nature Chemical Biology, vol. 11, No. 7, Jul. 2015, p. 448, XP055373184.

Harbers, "Wheat germ systems for cell-free protein expression," FEBS Letters, vol. 588, 2014, pp. 2762-2773.

Harrison et al., "Nogo-B receptor is necessary for cellular dolichol biosynthesis and protein N-glycosylation," The EMBO Journal, vol. 30, No. 12, 2011 (published online May 13, 2011), pp. 2490-2500.

Hillebrand et al., "Down-Regulation of Small Rubber Particle Protein Expression Affects Integrity of Rubber Particles and Rubber Content in Taraxacum brevicorniculatum," PLoS ONE, vol. 7, Issue 7, e41874, Jul. 23, 2012, pp. 1-9.

Hoffman et al., "The Who, What, and Where of Plant Polyprenol Biosynthesis Point to Thylakoid Membranes and Photosynthetic Performance," The Plant Cell, vol. 29, Jul. 2017, pp. 1552-1553.

International Preliminary Report on Patentability and Written Opinion of the International Searching Authority for International Application No. PCT/JP2017/041732, dated Jun. 25, 2019, with English translation.

International Search Report for International Application No. PCT/JP2016/065942, dated Jun. 28, 2016.

International Search Report for International Application No. PCT/JP2016/069172, dated Sep. 6, 2016, with English translation.

International Search Report for International Application No. PCT/JP2017/041732, dated Feb. 20, 2018.

Laibach et al., "Identification of a Taraxacum Brevicorniculatum Rubber Elongation Factor Protein that is Localized on Rubber Particles and Promotes Rubber Biosynthesis," The Plant Journal, vol. 82, 2015 (published online Mar. 24, 2015), pp. 609-620.

Madin et al., "A Highly Efficient and Robust Cell-free Protein Synthesis System Prepared from Wheat Embryos: Plants Apparently Contain a Suicide System Directed at Ribosomes," Proceedings of the National Academy of Sciences USA, vol. 97, No. 2, Jan. 18, 2000, pp. 559-564 (7 pages total).

Montoro et al., Biotechnologies in rubber tree (*Hevea brasiliensis*), Asian Pacific Conference on Tissue Culture and Agribiotechnology, Malaysia, Jun. 17-21, 2007, pp. 1-3.

Murota et al., "*Arabidopsis* Cell-Free Extract, ACE, a New In Vitro Translation System Derived from *Arabidopsis* Callus Cultures," Plant & Cell Physiology, vol. 52, No. 8, 2011, pp. 1443-1453.

Nguyen et al., "cis-Prenyltransferase Interacts with a Nogo-B Receptor Homolog for Dolichol Biosynthesis in Panax ginseng Meyer," Journal of Ginseng Research, vol. 41, 2017 (Available online Jan. 27, 2017), pp. 403-410.

Nozawa et al., "Chapter 17. Production of membrane proteins through the wheat-germ cell-free technology," Springer Protocol, Methods in Molecular Biology, 2010, pp. 213-218 (264 pages total).

Ohya et al., "Biosynthesis of Natural Rubber and Other Natural Polyisoprenoids," Biopolymers Online, Published online Jan. 15, 2005, 43 pages.

Park et al., "Mutation of Nogo-B receptor, a subunit of cis-prenyltransferase, causes a congenital disorder of glycosylation," Cell Metabolism, vol. 20, Sep. 2, 2014 (published Jul. 24, 2014), pp. 448-457.

Phatthiya et al., "Cloning and Expression of the Gene Encoding Solanesyl Diphosphate Synthase from Hevea Brasiliensis", Plant Science, vol. 172, 2007, pp. 824-831.

Post et al., "Laticifer-Specific cis-Prenyltransferase Silencing Affects the Rubber, Triterpene, and Inulin Content of Taraxacum brevicorniculatum," Plant Physiology, Mar. 2012, vol. 158, pp. 1406-1417.

Priya et al., "Differential expression pattern of rubber elongation factor (REF) mRNA transcripts from high and low yielding clones of rubber tree (*Hevea brasiliensis* Muell. Arg.)," Plant Cell Reports, vol. 26, 2007 (Published online Jul. 14, 2007), pp. 1833-1838.

Priya et al., "Molecular Cloning and Characterization of the Rubber Elongation Factor Gene and its Promoter Sequence from Rubber Tree (*Hevea brasiliensis*): a Gene Involved in Rubber Biosynthesis," Plant Science, vol. 171, 2006 (published online Jun. 13, 2006), pp. 470-480.

Qu et al., "A lettuce (*Lactuca sativa*) homolog of human Nogo-B receptor interacts with cis-prenyltransferase and is necessary for natural rubber biosynthesis," J. Biol. Chem., vol. 290, No. 4, Jan. 23, 2015, 2 pages, abstract provided only.

(56) References Cited

OTHER PUBLICATIONS

Rahman et al., "Draft genome sequence of the rubber tree *Hevea brasiliensis*," BMC Genomics, vol. 14, No. 75, 2013, pp. 1-15.

Rahman et al., "TSA: Hevea brasiliensis contig33814, mRNA sequence," Database GenBank [online], Accession No. JT945746, Feb. 5, 2013, pp. 1-2.

Results from BLAST(r) search for sequences producing significant alignments relative to Seq Id No. 1 in the GenBank, obtained on Jun. 28, 2021.

Results from BLAST(r) search for sequences producing significant alignments relative to Seq Id No. 3 in the GenBank, obtained on Jun. 28, 2021.

Results from BLAST(r) search for sequences producing significant alignments relative to Seq Id No. 5 in the GenBank, obtained on Jun. 28, 2021.

Rojruthai et al., "In Vitro Synthesis of High Molecular Weight Rubber by Hevea Small Rubber Particles," Journal of Bioscience and Bioengineering, vol. 109, No. 2, 2010 (Available online Sep. 18, 2009), pp. 107-114.

Sunderasan et al., "Incidence of Self- and Cross-pollination in Two Hevea brasilieness Clones," J. Nat. Rubb. Res. (1994), vol. 9, No. 4, pp. 253-257.

Surmacz et al., "cis-Prenyltransferase AtCPT6 produces a family of very short-chain polyisoprenoids in planta," Biochimica et Biophysica Acta, vol. 1841, 2014 (available online Dec. 1, 2013), pp. 240-250.

Takahashi et al., "Characterization of cis-prenyltransferases from the rubber producing plant *Hevea brasiliensis* heterologously expressed in yeast and plant cells," Plant Biotechnology, vol. 29, Oct. 20, 2012 (published online Aug. 30, 2012), pp. 411-417 (8 pages total).

Takahashi et al., "Molecular Insights of Natural Rubber Biosynthesis—an Approach from Prenyltransferase Gene Analysis", The Society of Rubber Science and Technology, vol. 76, No. 12, 2003, pp. 446-452, with 1 page abstract.

Tata et al., "Lacticifer Tissue-Specific Activation of the Hevea SRPP Promoter in Taraxacum brevicorniculatum and its Regulation by Light, Tapping and Cold Stress," Industrial Crops and Products, vol. 40, 2012, pp. 219-224.

Tian et al., "Hevea brasiliensis MYC1 (MYC1) gene, promoter region and 5' UTR," Chinese Academy of Tropical Agricultural Sciences, 2012, HM590649.

Unknown, "Successful in Vitro Synthesis of Natural Rubber by Bioengineering—Contributing to the Stable Supply of Natural Rubber with New Molecular Structure", Tohoku University, Nov. 16, 2016, 4 pages total.

Wang et al., "From Protein Sequence to Protein Function via Multi-Label Linear Discriminant Analysis," IEEE/ACM Transactions on Computational Biology and Bioinformatics, vol. 14, No. 3, 2017, pp. 503-513.

Xiang et al., "Proteome Analysis of the Large and the Small Rubber Particles of Hevea brasiliensis Using 2D-DIGE," Plant Physiology and Biochemistry, vol. 60, 2012 (Available online Sep. 5, 2012), pp. 207-213.

Yamashita et al., "Identification and Reconstitution of the Rubber Biosynthetic Machinery on Rubber Particles from Hevea Brasiliensis", eLife, vol. 5, No. 19022, Oct. 28, 2016, pp. 1-28.

Yokoyama, "Development of Membrane Protein-synthesizing System Without Using Cells", NPG Nature Asia-Pacific, vol. 7, No. 4-5, 2010, pp. 28-29, with English translation.

Zhao et al., "MYC genes with differential responses to tapping, mechanical wounding, ethrel and methyl jasmonate in laticifers of rubber tree (*Hevea brasiliensis* Muell. Arg.)," Journal of Plant Physiology, vol. 168, 2011, pp. 1649-1658.

* cited by examiner

FIG.1A

Without rubber particles (CPT not found on rubber particles)

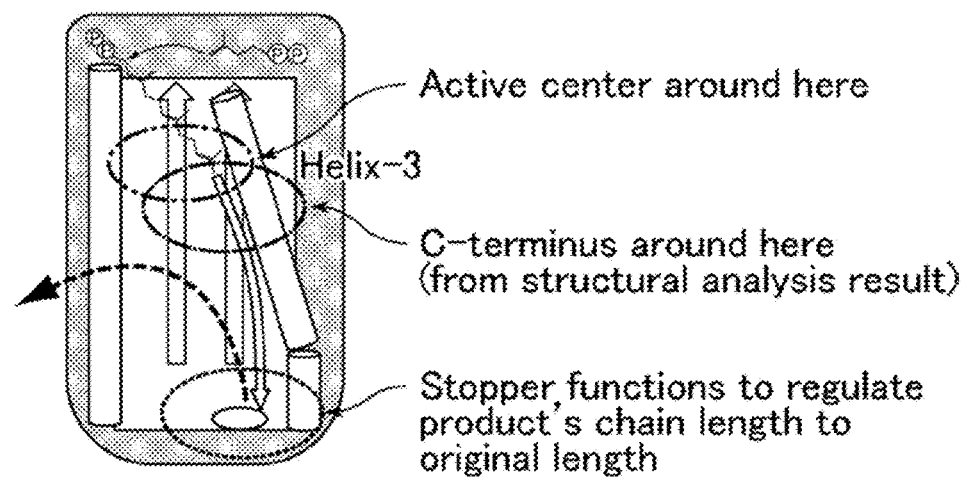

Active center around here

Helix-3

C-terminus around here
(from structural analysis result)

Stopper, functions to regulate
product's chain length to
original length

FIG.1B

With rubber particles (CPT not found on rubber particles)

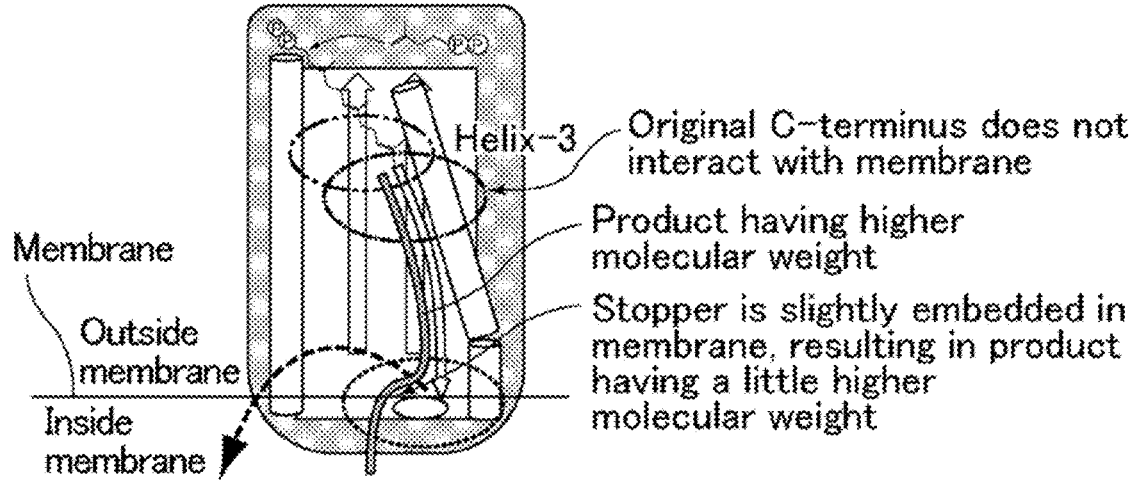

Helix-3    Original C-terminus does not
interact with membrane

Product having higher
molecular weight

Stopper is slightly embedded in
membrane, resulting in product
having a little higher
molecular weight Membrane Outside
membrane Inside
membrane With rubber particles (C-terminus-mutated CPT not found on rubber particles)

☐ Short- or medium-chain isoprene chain synthesis activity
■ Long-chain isoprene chain synthesis activity □ Short- or medium-chain isoprene chain synthesis activity
■ Long-chain isoprene chain synthesis activity

SEQUENCE LISTING

```
Sequence total quantity: 42
SEQ ID NO: 1           moltype = AA   length = 290
FEATURE                Location/Qualifiers
source                 1..290
                       mol_type = protein
                       organism = Hevea brasiliensis
SEQUENCE: 1
MELYNGERPS VFRLLGKYMR KGLYSILTQG PIPTHIAFIL DGNRRFAKKH KLPEGGGHKA   60
GFLALLNVLT YCYELGVKYA TIYAFSIDNF RRKPHEVQYV MDLMLEKIEG MIMEESIINA  120
YDICVRFVGN LKLLSEPVKT AADKIMRATA NNSKCVLLIA VCYTSTDEIV HAVEESSELN  180
```

```
SNEVCNNQEL EEANATGSGT VIQIENMESY SGIKLVDLEK NTYINPYPDV LIRTSGETRL    240
SNYLLWQTTN CILYSPHALW PEIGLRHVVW AVINFQRHYS YLEKHKEYLK              290

SEQ ID NO: 2            moltype = DNA   length = 873
FEATURE                 Location/Qualifiers
source                  1..873
                        mol_type = genomic DNA
                        organism = Hevea brasiliensis
SEQUENCE: 2
atggaattat acaacggtga gaggccaagt gtgttcagac ttttagggaa gtatatgaga    60
aaaagggttat atagcatcct aacccagggt cccatcccta ctcatattgc cttcatattg   120
gatgaaaca ggaggtttgc taagaagcat aaactgccag aaggaggtgg tcataaggct     180
ggattttag ctcttctgaa cgtactaact tattgctatg agttaggagt gaaatatgcg     240
actatctatg cctttagcat cgataatttt cgaaggaaac ctcatgaggt tcagtacgta    300
atggatctaa tgctggagaa gattgaaggg atgatcatgg aagaaagtat catcaatgca   360
tatgatattt gcgtacgttt tgtgggtaac ctgaagcttt taagtgagcc agtcaagacc   420
gcagcagata agattatgag ggctactgcc aacaattcca aatgtgtgct tctcattgct   480
gtatgctata cttcaactga tgagatcgtg catgctgttg aagaatcctc tgaattgaac   540
tccaatgaag tttgtaacaa tcaagaattg gaggaggcaa atgcaactgg aagcggtact   600
gtgattcaaa ttgagaacat ggagtcgtat tctggaataa aacttgtaga ccttgagaaa   660
aacacctaca taaatcctta tcctgatgtt ctgattcgaa cttctgggga gacccgtctg   720
agcaactact tactttggca gactactaat tgcatactgt attctcctca tgcactgtgg   780
ccagagattg gtcttcgaca cgtggtgtgg gcagtaatta acttccaacg tcattattct   840
tacttggaga aacataagga atacttaaaa taa                               873

SEQ ID NO: 3            moltype = AA   length = 302
FEATURE                 Location/Qualifiers
source                  1..302
                        mol_type = protein
                        organism = Arabidopsis thaliana
SEQUENCE: 3
MLSILSSLLS LLFLFIISCF FITSHFWFPL SLPKILGFIK ITSSRDDYDN EQRDEGTYVV    60
GVEELQRELM PRHVAVIMDG NRRWAKRAGL LTSQGHEAGA KRLIEFSELC FKLGIHTVSA   120
FAFSTENWGR HKIEVKCLMS LIQHYLKSKI QYFQREETRV SVIGNLTKIP ESLLRTVQEI   180
EEATRSYKKK HLILAIDYSG RLDILRACKS IVKKSEKGLI REEDVDEALI ERELLTNCTE   240
FPSPDLLIRT SGEQRISNFF LWQLAYTELF FSPVLWPDFD KDKLLEALVS YQRRERRFGC   300
RV                                                                 302

SEQ ID NO: 4            moltype = AA   length = 368
FEATURE                 Location/Qualifiers
source                  1..368
                        mol_type = protein
                        organism = Hevea brasiliensis
SEQUENCE: 4
MEIFEAGRPS VLASLGRFIR KCIFRILSIG PIPSHVAFIM DGNRRFAKKE KLEEGSGHRA    60
GSLALMSTLK YCYELGVKYV TIYAFSIDNF RRRPDEVQLI MDLILEKIEG LLRDENVVNA   120
YGIRVRFVGT LKLLSEPVRV AAEKVARASA KNTKFVLVIC IAYSSTDEIV HAVQESCKYK   180
LNKIEPSNSN RACNDANEQV EENGKKIDST ITHGVQESCK DETDKSRTIN AKPMYNGVTK   240
EAGGTDNANT VIVNSIGDKW DDAHELEATR TGNGVISVEE IDKMLSHSSI KLVDIEKKLH   300
MAVAPDPDIL VRTSGESRLS NFLLWQTSNC SLYSPKALWP EIGLRHLVWA VITFQRNHSY   360
LEKKKKQL                                                           368

SEQ ID NO: 5            moltype = DNA   length = 909
FEATURE                 Location/Qualifiers
source                  1..909
                        mol_type = genomic DNA
                        organism = Arabidopsis thaliana
SEQUENCE: 5
atgttgtcta ttctctcttc tcttttatct ctcctttttc tgtttatcat ctcttgtttc    60
ttcatcacaa gccatttttg gttccctctt tccttgccaa aaatactcgg attcatcaaa   120
atcacatctt cgagagacga ttatgacaac gagcaacgtg acgagggaac ttatgtggta   180
ggagtggagg agctacaaag agagctgatg ccaagacatg tggcagtgat aatggacgga   240
aaccggagat gggccaaacg ggccggattg ctgacgtcac aaggccacga ggccggagct   300
aaacggctta tagagttctc cgagctttgc tttaaattgg gaattcatac agttcagct    360
tttgccttct ccacagagaa ttggggaaga cacaagattg aggttaagtg cttgatgtct   420
ttgatccaac attacctcaa gtccaagatc caatatttcc aaagagagga aactcgagtt   480
tctgttatcg ggaacctaac gaagatccct gagtctctcc tccgaacagt ccaagagata   540
gaggaagcta cgagaagcta taagaagaag catctctcat tggcaatata ttacagcggg   600
agattagaca tcttgcgagc tgcaagagt attgtgaaga aatcagaaaa agggttgatc   660
cgagaggaag atgtagacga ggcattgatc gaaagagagc ttctgacaaa ttgtactgag   720
ttcccaagtc ctgatctatt gattaggaca agtggagaac agaggattag taacttcttc   780
ttgtggcaac ttgcttatac agagctcttc ttctcgccgg tcctttggcc tgatttcgat   840
aaggataagc ttctagaggc cctggtttcg tatcagcgcc gggaaagacg atttggctgt   900
cgggtttga                                                          909

SEQ ID NO: 6            moltype = DNA   length = 1107
FEATURE                 Location/Qualifiers
source                  1..1107
                        mol_type = genomic DNA
```

-continued

```
                         organism = Hevea brasiliensis
SEQUENCE: 6
atggaaatat ttgaggctgg taggccaagc gtgcttgcaa gtttggggag atttatcaga    60
aaatgcatat ttcgcattct atcaataggt cccatcccaa gtcatgttgc cttcataatg   120
gatggaaacc ggaggtttgc taagaaggag aaactggaag aaggatctgg tcacagggct   180
ggatctttag ctctaatgtc cacgcttaag tactgctatg agttgggagt gaagtatgtg   240
actatatatg ccttcagcat tgataatttt agaaggcgac ctgatgaggt tcagctcata   300
atggatctaa tactggagaa gattgagggg ctgctcaggg acgaaaatgt tgtcaatgca   360
tatggcatca gagtacgatt tgtaggtacc ttgaagcttc taagtgagcc agtcaggggt   420
gcagcagaaa aagtcgccag ggctagtgcc aagaatacca agtttgtgct tgtcatttgt   480
atagcctatt cttcaactga tgagattgtg catgctgttc aagaatcttg taaatataaa   540
ttgaacaaaa ttgagccatc taactccaac agggcttgca atgatgcgaa tgaacaagta   600
gaagaaaatg gtaagaagat agatagtacc atcacacatg gtgttcaaga atcctgcaaa   660
gatgaaacag ataaatctcg cacaataaac gcaaagccaa tgtataatgg tgtgaccaaa   720
gaagctggag ggactgacaa tgctaatact gtgatagtaa attccatcgg agacaagtgg   780
gatgatgctc acgaactgga ggcaactaga actggcaatg gtgtgatttc agtagaagaa   840
attgataaga tgctgtcaca ttctagcata aagctggtag acattgagaa aaaattgcac   900
atggctgtag cccctgatcc tgatatcttg gttcgaactt ctggagagag ccgtctgagc   960
aacttcctac tttggcagac tagtaactgt tcactgtatt ctccaaaggc actgtggccg  1020
gagattggcc tacgccactt ggtgtgggca gtaataacct tccaacgtaa tcattcttat  1080
ttggagaaga aaaagaagca gttgtaa                                      1107

SEQ ID NO: 7           moltype = AA   length = 306
FEATURE                Location/Qualifiers
source                 1..306
                       mol_type = protein
                       organism = synthetic construct
SEQUENCE: 7
MLSILSSLLS LLFLFIISCF FITSHFWFPL SLPKILGFIK ITSSRDDYDN EQRDEGTYVV    60
GVEELQRELM PRHVAVIMDG NRRWAKRAGL LTSQGHEAGA KRLIEFSELC FKLGIHTVSA   120
FAFSTENWGR HKIEVKCLMS LIQHYLKSKI QYFQREETRV SVIGNLTKIP ESLLRTVQEI   180
EEATRSYKKK HLILAIDYSG RLDILRACKS IVKKSEKGLI REEDVDEALI ERELLTNCTE   240
FPSPDLLIRT SGEQRISNFF LWQLAYTELF FSPVLWPDIG LRHVVWAVIN FQRHYSYLEK   300
HKEYLK                                                             306

SEQ ID NO: 8           moltype = AA   length = 369
FEATURE                Location/Qualifiers
source                 1..369
                       mol_type = protein
                       organism = synthetic construct
SEQUENCE: 8
MEIFEAGRPS VLASLGRFIR KCIFRILSIG PIPSHVAFIM DGNRRFAKKE KLEEGSGHRA    60
GSLALMSTLK YCYELGVKYV TIYAFSIDNF RRRPDEVQLI MDLILEKIEG LLRDENVVNA   120
YGIRVRFVGT LKLLSEPVRV AAEKVARASA KNTKFVLVIC IAYSSTDEIV HAVQESCKYK   180
LNKIEPSNSN RACNDANEQV EENGKKIDST ITHGVQESCK DETDKSRTIN AKPMYNGVTK   240
EAGGTDNANT VIVNSIGDKW DDAHELEATR TGNGVISVEE IDKMLSHSSI KLVDIEKKLH   300
MAVAPDPDIL VRTSGESRLS NFLLWQTSNC SLYSPKALWP EIGLRHVVWA VINFQRHYSY   360
LEKHKEYLK                                                          369

SEQ ID NO: 9           moltype = DNA   length = 921
FEATURE                Location/Qualifiers
source                 1..921
                       mol_type = other DNA
                       organism = synthetic construct
SEQUENCE: 9
atgttgtcta ttctctcttc tcttttatct ctcctttttc tgtttatcat ctcttgtttc    60
ttcatcacaa gccatttttg gttccctctt tccttgccaa aaatactcgg attcatcaaa   120
atcacatctt cgagagacga ttatgacaac gagcaacgtg acgagggaac ttatgtggta   180
ggagtggagg agctacaaag agagctgatg ccaagacatg tggcagtgat aatggacgga   240
aaccggaggt gggccaaacg ggccggattg ctgacgtcac aaggccacga ggccggagct   300
aaacggctta tagagttctc cgagctttgc tttaaattgg ggattcatac agtttcagct   360
tttgccttct ccacagagaa ttggggaaga cacaagattg aggttaagtg cttgatgtct   420
ttgatccaac attacctcaa gtccaagatc caatatttcc aaagagagga aactcgagtt   480
tctgttatcg ggaacctaac gaagatccct gagtctctcc tccgaacagt ccaagagata   540
gaggaagcta cgagaagcta taagaagaag catctcatat tggcaataga ttacagcggg   600
agattagaca tcttgcgagc ttgcaagagt attgtgaaga aatcagaaaa agggttgatc   660
cgagaggaag atgtagacga ggcattgatc gaaagagagc ttctgacaaa ttgtactgag   720
ttcccaagtc ctgatctatt gattaggaca agtggagaac agaggattag taacttcttc   780
ttgtggcaac ttgcttatac agagctcttc ttctcgccgg tcctttggcc tgatattggt   840
cttcgacacg tggtgtgggc agtaattaac ttccaacgtc attattctta cttggagaaa   900
cataaggaat acttaaaata a                                             921

SEQ ID NO: 10          moltype = DNA   length = 1110
FEATURE                Location/Qualifiers
source                 1..1110
                       mol_type = other DNA
                       organism = synthetic construct
SEQUENCE: 10
atggaaatat ttgaggctgg taggccaagc gtgcttgcaa gtttggggag atttatcaga    60
```

-continued

```
aaatgcatat ttcgcattct atcaataggt cccatcccaa gtcatgttgc cttcataatg  120
gatggaaacc ggaggtttgc taagaaggag aaactggaag aaggatctgg tcacagggct  180
ggatctttag ctctaatgtc cacgcttaag tactgctatg agttgggagt gaagtatgtg  240
actatatatg ccttcagcat tgataatttt agaaggcgac ctgatgaggt tcagctcata  300
atggatctaa tactggagaa gattgagggg ctgctcaggg gcgaaaatgt tgtcaatgca  360
tatggcatca gagtacgatt tgtaggtacc ttgaagcttc taagtgagcc agtcagggtc  420
gcagcagaaa aagtcgccag ggctagtgcc aagaatacca agtttgtgct tgtcatttgt  480
atagcctatt cttcaactga tgagattgtg catgctgttc aagaatcttg taaatataaa  540
ttgaacaaaa ttgagccatc taactccaac agggcttgca atgatgcgaa tgaacaagta  600
gaagaaaatg gtaagaagat agatagtacc atcacacatg gtgttcaaga atcctgcaaa  660
gatgaaacag ataaatctcg cacaataaac gcaaagccaa tgtataatgg tgtgaccaaa  720
gaagctggag ggactgacaa tgctaatact gtgatagtaa attccatcgg agacaagtgg  780
gatgatgctc acgaactgga ggcaactaga actggcaatg tgtgtgattc agtagaagaa  840
attgataaga tgctgtcaca ttctagcata aagctggtag acattgagaa aaaaattgcac  900
atggctgtag cccctgatcc tgatatcttg gttcgaactt ctggagagag ccgtctgagc  960
aacttcctac tttggcagac tagtaactgt tcactgtatt ctccaaaggc actgtggccg 1020
gagattggtc ttcgacacgt ggtgtgggca gtaattaact ccaacgtca ttattcttac 1080
ttggagaaac ataaggaata cttaaaataa                                   1110
```

SEQ ID NO: 11          moltype = DNA  length = 774
FEATURE                Location/Qualifiers
source                 1..774
                       mol_type = genomic DNA
                       organism = Hevea brasiliensis
SEQUENCE: 11

```
atggatttga aacctggagc tggagggcag agagttaatc gtttagtgga tccgattagt  60
tatcatttc ttcaatttct gtggcgtact ctacatcttc ttgtcagctt atggtacctt  120
caagttagta tggtccaaat gatcgaaggc tttctaatct ctagtggact tgtgaaacgc  180
tatggagccc tcgatattga caaggtccgg taccttgcca ttgtggtaga tagtgaagaa  240
gcttaccaaa tttctaaagt tattcagctt ttgaaatggg aggaagatat gggtgtgaaa  300
catttatgcc tctatgattc aaaaggagtt ctcaagacaa acaagaaaac catcatggag  360
agtttgaaca atgctatgcc atttgaggaa gcagttgaaa aagatgtttt actggaccag  420
aaacagatga ctgtggaatt tgcttccagc tccgatggaa aggaagcaat aaccagggca  480
gctaacgtac tctttatgaa gtatttgaag tatgctaaaa ctggtgtagg aaaggaagaa  540
ccatgcttta cagaagatca aatggatgag gcactaaaag ctataggtta caaagggccg  600
gaacctgact tgctattaat ttatggacct gttagatgcc atctaggttt ctcaccgtgg  660
agacttcgat atactgagat ggtgcatatg ggacccttga ggtacatgaa cctcggttca  720
ctaaaaaagg ccattcacag gttcacaaca gtgcagcaaa attatggtac atga          774
```

SEQ ID NO: 12          moltype = AA  length = 257
FEATURE                Location/Qualifiers
source                 1..257
                       mol_type = protein
                       organism = Hevea brasiliensis
SEQUENCE: 12

```
MDLKPGAGGQ RVNRLVDPIS YHFLQFLWRT LHLLVSLWYL QVSMVQMIEG FLISSGLVKR   60
YGALDIDKVR YLAIVVDSEE AYQISKVIQL LKWVEDMGVK HLCLYDSKGV LKTNKKTIME  120
SLNNAMPFEE AVEKDVLLDQ KQMTVEFASS SDGKEAITRA ANVLFMKYLK YAKTGVGKEE  180
PCFTEDQMDE ALKAIGYKGP EPDLLLIYGP VRCHLGFSPW RLRYTEMVHM GPLRYMNLGS  240
LKKAIHRFTT VQQNYGT                                                 257
```

SEQ ID NO: 13          moltype = DNA  length = 417
FEATURE                Location/Qualifiers
source                 1..417
                       mol_type = genomic DNA
                       organism = Hevea brasiliensis
SEQUENCE: 13

```
atggctgaag acgaagacaa ccaacaaggg caggggaggg ggttaaaata tttgggtttt   60
gtgcaagacg cggcaactta tgctgtgact accttctcaa acgtctatct ttttgccaaa  120
gacaaatctg gtccactgca gcctggtgtc gatatcattg agggtccggt gaagaacgtg  180
gctgtacctc tctataatag gttcagttat attcccaatg gagctctcaa gtttgtagac  240
agcacggttg ttgcatctgt cactattata gatcgctctc ttcccccaat tgtcaaggac  300
gcatctatcc aagttgtttc agcaattcga gctgccccag aagctgctcg ttctctggct  360
tcttctttgc ctgggcagac caagatactt gctaaggtgt tttatggaga gaattga      417
```

SEQ ID NO: 14          moltype = AA  length = 138
FEATURE                Location/Qualifiers
source                 1..138
                       mol_type = protein
                       organism = Hevea brasiliensis
SEQUENCE: 14

```
MAEDEDNQQG QGEGLKYLGF VQDAATYAVT TFSNVYLFAK DKSGPLQPGV DIIEGPVKNV   60
AVPLYNRFSY IPNGALKFVD STVVASVTII DRSLPPIVKD ASIQVVSAIR AAPEAARSLA  120
SSLPGQTKIL AKVFYGEN                                                138
```

SEQ ID NO: 15          moltype = DNA  length = 34
FEATURE                Location/Qualifiers
misc_feature           1..34
                       note = PRIMER-1

-continued

```
source                 1..34
                       mol_type = other DNA
                       organism = synthetic construct
SEQUENCE: 15
tttggatccg atggaattat acaacggtga gagg                              34

SEQ ID NO: 16          moltype = DNA   length = 39
FEATURE                Location/Qualifiers
misc_feature           1..39
                       note = PRIMER-2
source                 1..39
                       mol_type = other DNA
                       organism = synthetic construct
SEQUENCE: 16
tttgcggccg cttattttaa gtattcctta tgtttctcc                         39

SEQ ID NO: 17          moltype = DNA   length = 31
FEATURE                Location/Qualifiers
misc_feature           1..31
                       note = PRIMER-3
source                 1..31
                       mol_type = other DNA
                       organism = synthetic construct
SEQUENCE: 17
tttctcgaga tggatttgaa acctggagct g                                 31

SEQ ID NO: 18          moltype = DNA   length = 33
FEATURE                Location/Qualifiers
misc_feature           1..33
                       note = PRIMER-4
source                 1..33
                       mol_type = other DNA
                       organism = synthetic construct
SEQUENCE: 18
tttctcgagt catgtaccat aattttgctg cac                               33

SEQ ID NO: 19          moltype = DNA   length = 27
FEATURE                Location/Qualifiers
misc_feature           1..27
                       note = PRIMER-5
source                 1..27
                       mol_type = other DNA
                       organism = synthetic construct
SEQUENCE: 19
tttctcgaga tggctgaaga cgaagac                                      27

SEQ ID NO: 20          moltype = DNA   length = 28
FEATURE                Location/Qualifiers
misc_feature           1..28
                       note = PRIMER-6
source                 1..28
                       mol_type = other DNA
                       organism = synthetic construct
SEQUENCE: 20
tttggatcct caattctctc cataaaac                                     28

SEQ ID NO: 21          moltype = DNA   length = 32
FEATURE                Location/Qualifiers
misc_feature           1..32
                       note = PRIMER-7
source                 1..32
                       mol_type = other DNA
                       organism = synthetic construct
SEQUENCE: 21
gtgctggaat tcatggaaat atttgaggct gg                                32

SEQ ID NO: 22          moltype = DNA   length = 61
FEATURE                Location/Qualifiers
misc_feature           1..61
                       note = PRIMER-8
source                 1..61
                       mol_type = other DNA
                       organism = synthetic construct
SEQUENCE: 22
aagcttgtcg acttaatggt gatggtgatg atgaccggta cgcaactgct tctttttctt  60
c                                                                  61

SEQ ID NO: 23          moltype = DNA   length = 46
FEATURE                Location/Qualifiers
```

-continued

```
misc_feature           1..46
                       note = PRIMER-9
source                 1..46
                       mol_type = other DNA
                       organism = synthetic construct
SEQUENCE: 23
acatcaccaa gatatcatgt tgtctattct ctcttctctt ttatct                          46

SEQ ID NO: 24          moltype = DNA  length = 26
FEATURE                Location/Qualifiers
misc_feature           1..26
                       note = PRIMER-10
source                 1..26
                       mol_type = other DNA
                       organism = synthetic construct
SEQUENCE: 24
gtcgaagacc aatatcaggc caaagg                                                26

SEQ ID NO: 25          moltype = DNA  length = 36
FEATURE                Location/Qualifiers
misc_feature           1..36
                       note = PRIMER-11
source                 1..36
                       mol_type = other DNA
                       organism = synthetic construct
SEQUENCE: 25
acatcaccaa gatatcatgg aaatatttga ggctgg                                     36

SEQ ID NO: 26          moltype = DNA  length = 20
FEATURE                Location/Qualifiers
misc_feature           1..20
                       note = PRIMER-12
source                 1..20
                       mol_type = other DNA
                       organism = synthetic construct
SEQUENCE: 26
gaagaccaat ctccggccac                                                       20

SEQ ID NO: 27          moltype = DNA  length = 26
FEATURE                Location/Qualifiers
misc_feature           1..26
                       note = PRIMER-13
source                 1..26
                       mol_type = other DNA
                       organism = synthetic construct
SEQUENCE: 27
cctttggcct gatattggtc ttcgac                                                26

SEQ ID NO: 28          moltype = DNA  length = 27
FEATURE                Location/Qualifiers
misc_feature           1..27
                       note = PRIMER-14
source                 1..27
                       mol_type = other DNA
                       organism = synthetic construct
SEQUENCE: 28
tacaggtttt cctcgagtta ttttaag                                               27

SEQ ID NO: 29          moltype = DNA  length = 20
FEATURE                Location/Qualifiers
misc_feature           1..20
                       note = PRIMER-15
source                 1..20
                       mol_type = other DNA
                       organism = synthetic construct
SEQUENCE: 29
gtggccggag attggtcttc                                                       20

SEQ ID NO: 30          moltype = DNA  length = 27
FEATURE                Location/Qualifiers
misc_feature           1..27
                       note = PRIMER-16
source                 1..27
                       mol_type = other DNA
                       organism = synthetic construct
SEQUENCE: 30
tacaggtttt cctcgagtta ttttaag                                               27

SEQ ID NO: 31          moltype = DNA  length = 46
```

-continued

```
FEATURE                 Location/Qualifiers
misc_feature            1..46
                        note = PRIMER-17
source                  1..46
                        mol_type = other DNA
                        organism = synthetic construct
SEQUENCE: 31
acatcaccaa gatatcatgt tgtctattct ctcttctctt ttatct                      46

SEQ ID NO: 32           moltype = DNA   length = 28
FEATURE                 Location/Qualifiers
misc_feature            1..28
                        note = PRIMER-18
source                  1..28
                        mol_type = other DNA
                        organism = synthetic construct
SEQUENCE: 32
tgattggccg aggcggcctt attttaag                                          28

SEQ ID NO: 33           moltype = DNA   length = 36
FEATURE                 Location/Qualifiers
misc_feature            1..36
                        note = PRIMER-19
source                  1..36
                        mol_type = other DNA
                        organism = synthetic construct
SEQUENCE: 33
acatcaccaa gatatcatgg aaatatttga ggctgg                                 36

SEQ ID NO: 34           moltype = DNA   length = 28
FEATURE                 Location/Qualifiers
misc_feature            1..28
                        note = PRIMER-20
source                  1..28
                        mol_type = other DNA
                        organism = synthetic construct
SEQUENCE: 34
tgattggccg aggcggcctt attttaag                                          28

SEQ ID NO: 35           moltype = DNA   length = 46
FEATURE                 Location/Qualifiers
misc_feature            1..46
                        note = PRIMER-21
source                  1..46
                        mol_type = other DNA
                        organism = synthetic construct
SEQUENCE: 35
acatcaccaa gatatcatgt tgtctattct ctcttctctt ttatct                      46

SEQ ID NO: 36           moltype = DNA   length = 35
FEATURE                 Location/Qualifiers
misc_feature            1..35
                        note = PRIMER-22
source                  1..35
                        mol_type = other DNA
                        organism = synthetic construct
SEQUENCE: 36
tgattggccg aggcggcctc aaacccgaca gccaa                                  35

SEQ ID NO: 37           moltype = DNA   length = 36
FEATURE                 Location/Qualifiers
misc_feature            1..36
                        note = PRIMER-23
source                  1..36
                        mol_type = other DNA
                        organism = synthetic construct
SEQUENCE: 37
acatcaccaa gatatcatgg aaatatttga ggctgg                                 36

SEQ ID NO: 38           moltype = DNA   length = 39
FEATURE                 Location/Qualifiers
misc_feature            1..39
                        note = PRIMER-24
source                  1..39
                        mol_type = other DNA
                        organism = synthetic construct
SEQUENCE: 38
tgattggccg aggcggccta caactgcttc tttttcttc                              39
```

-continued

```
SEQ ID NO: 39          moltype = DNA   length = 46
FEATURE                Location/Qualifiers
misc_feature           1..46
                       note = PRIMER-25
source                 1..46
                       mol_type = other DNA
                       organism = synthetic construct
SEQUENCE: 39
acatcaccaa gatatcatgt tgtctattct ctcttctctt ttatct                    46

SEQ ID NO: 40          moltype = DNA   length = 28
FEATURE                Location/Qualifiers
misc_feature           1..28
                       note = PRIMER-26
source                 1..28
                       mol_type = other DNA
                       organism = synthetic construct
SEQUENCE: 40
tgattggccg aggcggcctt attttaag                                        28

SEQ ID NO: 41          moltype = DNA   length = 36
FEATURE                Location/Qualifiers
misc_feature           1..36
                       note = PRIMER-27
source                 1..36
                       mol_type = other DNA
                       organism = synthetic construct
SEQUENCE: 41
acatcaccaa gatatcatgg aaatatttga ggctgg                               36

SEQ ID NO: 42          moltype = DNA   length = 28
FEATURE                Location/Qualifiers
misc_feature           1..28
                       note = PRIMER-28
source                 1..28
                       mol_type = other DNA
                       organism = synthetic construct
SEQUENCE: 42
tgattggccg aggcggcctt attttaag                                        28
```

METHOD FOR PRODUCING POLYISOPRENOID BY REACTION CATALYZED BY MUTANT CIS-PRENYLTRANSFERASE (CPT) FAMILY PROTEIN, AND METHOD FOR PRODUCING RUBBER PRODUCT

REFERENCE TO ELECTRONIC SEQUENCE LISTING

The application contains a Sequence Listing which has been submitted electronically in .XML format and is hereby incorporated by reference in its entirety. Said .XML copy, created on Jan. 31, 2023, is named "5051-0555PUS1.xml" and is 56,700 bytes in size. The sequence listing contained in this .XML file is part of the specification and is hereby incorporated by reference herein in its entirety.

TECHNICAL FIELD

The present disclosure relates to a mutant cis-prenyltransferase (CPT) family protein, a method for producing a polyisoprenoid, a vector, a transgenic plant, a method for producing a pneumatic tire, and a method for producing a rubber product.

BACKGROUND ART

It is known for a cis-prenyltransferase (CPT) family protein of human origin that the interaction between the N-terminus of the CPT family protein (hereinafter, also referred to simply as CPT) and a Nogo-B receptor (NgBR) family protein (corresponding to HRBP derived from rubber trees) is important for the CPT activity.

It is also known that a cis-prenyltransferase (CPT) family protein found on rubber particles (hereinafter, also referred to simply as rubber synthase) loses its enzymatic activity when it is a N-terminus-deficient rubber synthase. In other words, the N-terminus of the rubber synthase is known to be a site that is important for enzymatic activity. However, conventional techniques have room for improvement in producing a high molecular weight polyisoprenoid.

SUMMARY OF DISCLOSURE

Technical Problem

The present disclosure aims to solve the above-mentioned problem and provide a mutant cis-prenyltransferase (CPT) family protein and a method for producing a polyisoprenoid, which enable the production of a high molecular weight polyisoprenoid.

The present disclosure also aims to solve the above-mentioned problem and provide a vector which enables the production of a high molecular weight polyisoprenoid when it is introduced into a plant by genetic recombination techniques, as well as a transgenic plant into which the vector has been introduced.

Solution to Problem

The present disclosers believe that Nogo-B receptor (NgBR) family proteins serve to assist CPT to be folded in the correct conformation. Thus, if CPT loses its interaction with NgBR, it is less likely to be folded in the correct conformation and may lose its enzymatic activity.

Studies of the present disclosers have found the following.

Finding 1: Rubber Synthesis on Rubber Particles Using Wild-Type CPT

It has been found that when CPT without any mutation is directly bound to rubber particles to synthesize a polyisoprenoid, no high molecular weight polyisoprenoid may be synthesized on the rubber particles, depending on the type of CPT. Particularly when a short- or medium-chain isoprenoid synthase is used which inherently does not bind to the membrane, there is, in the first place, a problem in that it cannot bind to the membrane.

Finding 2: Polyisoprenoid Synthesis on Membrane Particles Using Enzyme Obtained by Fusing CPT to Peptide (or Enzyme) that Assists Membrane Binding As a solution to the problem of the finding 1, the disclosers tried to fuse a peptide or enzyme that assists membrane-binding ability (e.g., a membrane-binding part of a lipid droplet-associated protein or SRPP capable of binding to rubber particles) to the N-terminal or C-terminal side of CPT. However, although this method solves the membrane-binding ability problem of the enzyme, it leaves the possibility that the enzyme may not be correctly embedded in the membrane or that the fusion protein may inhibit the interaction with NgBR which is considered to be important for the enzymatic activity.

The present disclosers have made extensive studies and arrived at the idea that the synthesis of a high molecular weight polyisoprenoid on rubber particles requires: correct folding of CPT (guideline a), binding thereof to the membrane (guideline b), and correct (deep) incorporation thereof into the membrane (guideline c).

As a result of extensive studies, the present disclosers have found that the technique of the finding 1 faces challenges with respect to the guidelines b and c when CPT not naturally found on rubber particles is used, while the technique of the finding 2 can solve the guideline b by fusion to a membrane-binding peptide but faces challenges with respect to the guideline a (when the peptide is fused to the N-terminal side, the enzyme is not successfully folded), and the guideline c (when the peptide is fused to the C-terminal side, the enzyme is not correctly incorporated into the membrane) due to the negative effect of the peptide fusion.

While investigating the relationship between the terminal structure of CPT and the interaction with NgBR, the present disclosers have found that the C-terminal structure of CPT affects the ability to bind to the membrane. Thus, the present disclosers have made studies on a technique for incorporating the enzyme deeply into the membrane by changing the C-terminal structure without changing the N-terminal structure involved in correct folding of CPT. Then, the present disclosers have arrived at a technique for incorporating the enzyme deeply into the membrane by using the C-terminal structure of CPT found on rubber particles. Here, it has been found that CPT not found on rubber particles may be correctly incorporated into the membrane by swapping the C-terminal sequence of the CPT not found on rubber particles with the C-terminal sequence of CPT found on rubber particles, rather than by fusing the C-terminal sequence of CPT found on rubber particles to the C-terminus of the former CPT. These findings have led to the completion of the present disclosure.

Specifically, the present disclosure relates to a mutant cis-prenyltransferase (CPT) family protein, obtained by mutating an amino acid sequence of a C-terminal region of a cis-prenyltransferase (CPT) family protein not found on rubber particles to be identical or similar to an amino acid sequence of a C-terminal region of a cis-prenyltransferase (CPT) family protein found on rubber particles. Hereinafter, this disclosure is taken as a first aspect of the present disclosure and may be referred to as the first disclosure.

Advantageous Effects of Disclosure

The mutant cis-prenyltransferase (CPT) family protein according to the first disclosure is obtained by mutating the amino acid sequence of a C-terminal region of a cis-prenyltransferase (CPT) family protein not found on rubber particles to be identical or similar to the amino acid sequence of a C-terminal region of a cis-prenyltransferase (CPT) family protein found on rubber particles. This mutant cis-prenyltransferase (CPT) family protein enables the production of a higher molecular weight polyisoprenoid than that produced with the unmutated cis-prenyltransferase (CPT) family protein. Thus, a method for producing a polyisoprenoid using the mutant cis-prenyltransferase (CPT) family protein enables the production of a higher molecular weight polyisoprenoid than that produced with the unmutated cis-prenyltransferase (CPT) family protein.

A method for producing a pneumatic tire according to the first disclosure includes: producing a polyisoprenoid by the method for producing a polyisoprenoid of the first disclosure; kneading the polyisoprenoid with an additive to obtain a kneaded mixture; building a green tire from the kneaded mixture; and vulcanizing the green tire. With this method, which produces a pneumatic tire from a high molecular weight polyisoprenoid, it is possible to use plant resources effectively to environmentally friendly produce a pneumatic tire having excellent performance.

A method for producing a rubber product according to the first disclosure includes: producing a polyisoprenoid by the method for producing a polyisoprenoid of the first disclosure; kneading the polyisoprenoid with an additive to obtain a kneaded mixture; forming a raw rubber product from the kneaded mixture; and vulcanizing the raw rubber product. With this method, which produces a rubber product from a high molecular weight polyisoprenoid, it is possible to use plant resources effectively to environmentally friendly produce a rubber product having excellent performance.

A vector according to a second aspect of the present disclosure (hereinafter, also referred to as the second disclosure) contains a gene coding for the mutant cis-prenyltransferase (CPT) family protein of the first disclosure. Then, when the vector is introduced into a plant, the gene coding for the mutant cis-prenyltransferase (CPT) family protein of the first disclosure in the vector will be expressed to enable the production of a higher molecular weight polyisoprenoid in the plant as compared to before the gene recombination.

A method for producing a pneumatic tire according to the second disclosure includes: producing a polyisoprenoid using a transgenic plant produced by introducing the vector of the second disclosure into a plant; kneading the polyisoprenoid with an additive to obtain a kneaded mixture; building a green tire from the kneaded mixture; and vulcanizing the green tire. With this method, which produces a pneumatic tire from a high molecular weight polyisoprenoid produced by a transgenic plant that is enabled to produce a higher molecular weight polyisoprenoid as compared to before the gene recombination, it is possible to use plant resources effectively to environmentally friendly produce a pneumatic tire having excellent performance.

A method for producing a rubber product according to the second disclosure includes: producing a polyisoprenoid using a transgenic plant produced by introducing the vector of the second disclosure into a plant; kneading the polyisoprenoid with an additive to obtain a kneaded mixture; forming a raw rubber product from the kneaded mixture; and vulcanizing the raw rubber product. With this method, which produces a rubber product from a high molecular weight polyisoprenoid produced by a transgenic plant that is enabled to produce a higher molecular weight polyisoprenoid as compared to before the gene recombination, it is possible to use plant resources effectively to environmentally friendly produce a rubber product having excellent performance.

BRIEF DESCRIPTION OF DRAWINGS

FIG. 1A to FIG. 1C each show a schematic diagram of a possible mechanism.

DESCRIPTION OF EMBODIMENTS

Figure 1C:
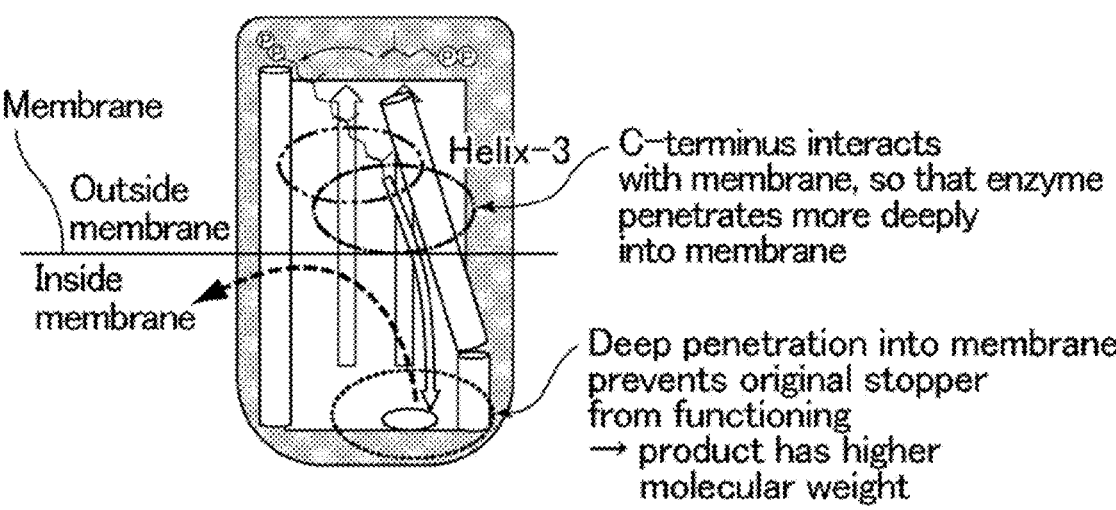

Herein, the first disclosure and the second disclosure are also referred collectively to as the present disclosure. The first disclosure will be described first, and the second disclosure will be described later.
(First Disclosure)
The mutant cis-prenyltransferase (CPT) family protein of the first disclosure is a mutant cis-prenyltransferase (CPT) family protein obtained by mutating the amino acid sequence of a C-terminal region of a cis-prenyltransferase (CPT) family protein not found on rubber particles to be identical or similar to the amino acid sequence of a C-terminal region of a cis-prenyltransferase (CPT) family protein found on rubber particles. This mutant cis-prenyltransferase (CPT) family protein enables the production of a higher molecular weight polyisoprenoid than that produced with the unmutated cis-prenyltransferase (CPT) family protein. Thus, a method for producing a polyisoprenoid using the mutant cis-prenyltransferase (CPT) family protein enables the production of a higher molecular weight polyisoprenoid than that produced with the unmutated cis-prenyltransferase (CPT) family protein.

Herein, the N-terminus of a protein refers to the amino terminus of the polypeptide chain, and the C-terminus of a protein refers to the carboxy terminus of the polypeptide chain.

The reason why the present disclosure provides the aforementioned advantageous effect is believed to be as follows.

As described earlier, the present disclosers have focused on the C-terminus of CPT. The importance of the C-terminus of CPT is higher for CPT not naturally found on rubber particles than for CPT found on rubber particles.

Other studies have also focused on the N-terminus of CPT, while studies on the role of the C-terminus have reported that mutation of the C-terminal $R_XG$ motif in homodimeric CPT can greatly reduce the activity. Structural findings have suggested that a C-terminal region may approach the substrate-binding site of another subunit to maintain the binding of a substrate. Meanwhile, it has been reported that the C-terminus of cPTL in heteromeric CPT functions similar to the $R_XG$ motif, but the function of the C-terminus of the CPT bound to cPTL is unknown. Actually, mutation of the C-terminus of a rubber synthase caused no significant change.

(1) Wild-type HRT1 (a CPT family protein found on rubber particles derived from *Hevea brasiliensis* (rubber synthase)), when bound to rubber particles, showed activity with no problem.

(2) N-terminus-deficient HRT1 was confirmed to bind to rubber particles, but no enzymatic activity was confirmed. This is consistent with the previous findings.

(3) C-terminus-mutated HRT1 bound to rubber particles showed activity with no problem.

These results reveal that the importance of the C-terminal structure is low for a CPT family protein found on rubber particles (rubber synthase).

In contrast, mutation of the C-terminus of CPT not found on rubber particles had a great impact.

(4) When wild-type HbCPT5 (CPT not found on rubber particles derived from *Hevea brasiliensis*) was bound to rubber particles, short isoprene chains were mainly synthesized.

(5) No significant change was observed in mutated HbCPT5 with N-terminal HRT1 (HbCPT5 in which the N-terminus has been substituted by the N-terminus of HRT1).

(6) When mutated HbCPT5 with C-terminal HRT1 (HbCPT5 in which the C-terminus has been substituted by the C-terminus of HRT1) was bound to rubber particles, the proportion of the product chains elongated to the rubber chain length was increased, thus confirming an increase in the production of a high molecular weight polyisoprenoid.

A comparison between the result (3) and the result (6) suggests that attaching a structure similar to the C-terminus of HRT1 (CPT found on rubber particles) to the C-terminus of CPT not found on rubber particles may be particularly effective when it is desired to bind CPT not naturally found on rubber particles to rubber particles to produce a high molecular weight product. A phenomenon similar to this effect was also observed in another CPT not found on rubber particles other than HbCPT5, AtCPT5 (CPT not found on rubber particles derived from *Arabidopsis thaliana*).

How the mutation of the C-terminus of CPT not found on rubber particles provides the effect is not clearly known, but it is believed from the following points that the mutation may serve to assist the CPT to enter deeply into the membrane.

In a test of interaction between mutated AtCPT5 with C-terminal HRT1 (AtCPT5 in which the C-terminus has been substituted by the C-terminus of HRT1) and HRBP (NgBR derived from *Hevea brasiliensis*), no interaction was observed.

In mutated AtCPT5 with C-terminal HRT1, the chain length regulation mechanism did not function well, despite no mutation of Helix2 and Helix3 which determine the chain length of the product. Therefore, an increase in the molecular weight of the product was observed.

It is known that the C-terminal structure of CPT is located close to the active center.

Thus, it is believed based on these findings that as the structure (for example, the degree of hydrophobicity) of the C-terminus, which is located close to the active center, is changed, the CPT is allowed to enter deeply into the membrane close to the active center.

The above possible mechanisms will be described using FIG. 1A to FIG. 1C.

FIG. 1A shows a schematic diagram of a reaction of CPT not found on rubber particles when it is not bound to rubber particles. In this case, due to the presence of a stopper, the chain length regulation mechanism functions so that a polyisoprenoid having a predetermined molecular weight can be produced.

FIG. 1B shows a schematic diagram of a reaction of CPT not found on rubber particles when it is bound to rubber particles. In this case, the stopper is slightly embedded in the rubber particles (membrane), and thus a polyisoprenoid can be produced which has a molecular weight a little higher than that produced when the CPT is not bound to rubber particles.

FIG. 1C shows a schematic diagram of a reaction of "a mutant CPT obtained by substituting a C-terminal region of CPT not found on rubber particles with a C-terminal region of CPT found on rubber particles" when it is bound to rubber particles. In this case, the C-terminus of the mutant CPT can interact with the rubber particles (membrane), and thus the CPT can enter more deeply into the rubber particles (membrane), so that the original stopper cannot function, resulting in a product having a higher molecular weight. Here, in the present disclosure, no fusion is performed to add an additional amino acid to a C-terminal region of CPT not found on rubber particles, but substitution of a C-terminal region of CPT not found on rubber particles is performed. Thus, it is believed that the above-mentioned mechanism can be more suitably achieved.

The reason why the importance of the C-terminus of CPT found on rubber particles is low is considered to be because the CPT found on rubber particles is an enzyme that originally binds to rubber particles and thus might have another part other than the C-terminus which binds to rubber particles (membrane). Hence, it is believed that even if the C-terminus of the CPT found on rubber particles does not function well, the other part may assist the binding to rubber particles (membrane).

Moreover, it is believed that as the CPT found on rubber particles contains no stopper that regulates the chain length of the product, a little shallow binding to rubber particles (membrane) may have little impact.

Accordingly, when a mutant CPT family protein obtained by mutating (substituting) a C-terminal region of a CPT family protein not found on rubber particles to be identical or similar to a C-terminal region of a CPT family protein found on rubber particles is used, the C-terminus of the mutant CPT can interact with rubber particles (membrane), and thus the CPT can enter more deeply into the rubber particles (membrane), so that the original stopper cannot function, resulting in a product having a higher molecular weight.

Thus, as the mutant CPT family protein of the first disclosure is obtained by mutating the amino acid sequence of a C-terminal region of a CPT family protein not found on rubber particles to be identical or similar to the amino acid sequence of a C-terminal region of a CPT family protein found on rubber particles, such a mutant CPT family protein enables the production of a higher molecular weight polyisoprenoid than that produced with the unmutated CPT family protein. Then, a method for producing a polyisoprenoid using the mutant CPT family protein enables the production of a higher molecular weight polyisoprenoid than that produced with the unmutated CPT family protein.

<Mutant Cis-Prenyltransferase (CPT) Family Protein>

The mutant cis-prenyltransferase (CPT) family protein of the present disclosure is obtained by mutating the amino acid sequence of a C-terminal region of a cis-prenyltransferase (CPT) family protein not found on rubber particles to be identical or similar to the amino acid sequence of a C-terminal region of a cis-prenyltransferase (CPT) family protein found on rubber particles.

Specifically, the mutant CPT family protein of the present disclosure is obtained by substituting the amino acid sequence of a C-terminal region of a cis-prenyltransferase (CPT) family protein not found on rubber particles with an amino acid sequence that is identical or similar to the amino acid sequence of a C-terminal region of a cis-prenyltransferase (CPT) family protein found on rubber particles.

The amino acid sequence of the C-terminal region of the cis-prenyltransferase (CPT) family protein not found on rubber particles is preferably a C-terminus-containing amino acid sequence within 50 amino acids upstream of the C-terminus of the protein, more preferably a C-terminus-containing amino acid sequence within 45 amino acids upstream of the C-terminus of the protein, still more preferably a C-terminus-containing amino acid sequence within 40 amino acids upstream of the C-terminus of the protein, particularly preferably a C-terminus-containing amino acid sequence within 35 amino acids upstream of the C-terminus of the protein, most preferably a C-terminus-containing amino acid sequence within 30 amino acids upstream of the C-terminus of the protein.

Herein, the amino acid sequence of the C-terminal region is a continuous amino acid sequence.

The amino acid sequence of the C-terminal region of the cis-prenyltransferase (CPT) family protein not found on rubber particles corresponds to, for example, positions 278 to 302 of the amino acid sequence of AtCPT5 derived from *Arabidopsis thaliana* represented by SEQ ID NO:3, or positions 342 to 368 of the amino acid sequence of HbCPT5 derived from *Hevea brasiliensis* represented by SEQ ID NO:4.

Likewise, the amino acid sequence of the C-terminal region of the cis-prenyltransferase (CPT) family protein found on rubber particles is preferably a C-terminus-containing amino acid sequence within 50 amino acids upstream of the C-terminus of the protein, more preferably a C-terminus-containing amino acid sequence within 45 amino acids upstream of the C-terminus of the protein, still more preferably a C-terminus-containing amino acid sequence within 40 amino acids upstream of the C-terminus of the protein, particularly preferably a C-terminus-containing amino acid sequence within 35 amino acids upstream of the C-terminus of the protein, most preferably a C-terminus-containing amino acid sequence within 30 amino acids upstream of the C-terminus of the protein.

The amino acid sequence of the C-terminal region of the cis-prenyltransferase (CPT) family protein found on rubber particles corresponds to, for example, positions 263 to 290 of the amino acid sequence of HRT1 derived from *Hevea brasiliensis* represented by SEQ ID NO:1.

The amino acid sequence similar to the amino acid sequence of the C-terminal region of the cis-prenyltransferase (CPT) family protein found on rubber particles is preferably an amino acid sequence having at least 80% sequence identity, more preferably at least 85% sequence identity, still more preferably at least 90% sequence identity, particularly preferably at least 95% sequence identity, most preferably at least 98% sequence identity, further most preferably at least 99% sequence identity to the amino acid sequence identical to the amino acid sequence of the C-terminal region of the cis-prenyltransferase (CPT) family protein found on rubber particles.

The mutation (substitution) of the amino acid sequence may be carried out by known techniques. Examples include homologous recombination, overlap extension PCR, infusion cloning, and fusion of PCR products using restriction enzymes.

The amino acid sequence of a N-terminal region of the mutant CPT family protein is preferably an amino acid sequence having at least 80% sequence identity, more preferably at least 85% sequence identity, still more preferably at least 90% sequence identity, particularly preferably at least 95% sequence identity, most preferably at least 98% sequence identity, even most preferably at least 99% sequence identity, further most preferably 100% sequence identity (no change in the N-terminal structure) to the amino acid sequence of a N-terminal region of the CPT family protein not found on rubber particles.

<<Cis-Prenyltransferase (CPT) Family Protein Found on Rubber Particles>>

The cis-prenyltransferase (CPT) family protein found on rubber particles may be any CPT family protein found on rubber particles and may be, for example, a cis-prenyltransferase (CPT) family protein found on rubber particles of plant origin. In particular, it is preferably a cis-prenyltransferase (CPT) family protein found on rubber particles derived from a plant of the genus *Hevea* or *Taraxacum* (particularly a plant of the genus *Hevea*), more preferably a cis-prenyltransferase (CPT) family protein found on rubber particles derived from *Hevea brasiliensis* or *Taraxacum kok-saghyz* (particularly *Hevea brasiliensis*).

Non-limiting examples of the plant include: the genus *Hevea*, e.g., *Hevea brasiliensis*; the genus *Sonchus*, e.g., *Sonchus oleraceus*, *Sonchus asper*, and *Sonchus brachyotus*; the genus *Solidago*, e.g., *Solidago altissima*, *Solidago virgaurea* subsp. *asiatica*, *Solidago virgaurea* subsp. *leipcarpa*, *Solidago virgaurea* subsp. *leipcarpa* f. *paludosa*, *Solidago virgaurea* subsp. *gigantea*, and *Solidago gigantea* Ait. var. *leiophylla Fernald*; the genus *Helianthus*, e.g., *Helianthus annuus*, *Helianthus argophyllus*, *Helianthus atrorubens*, *Helianthus debilis*, *Helianthus decapetalus*, and *Helianthus giganteus*; the genus *Taraxacum*, e.g., dandelion (*Taraxacum*), *Taraxacum venustum* H. *Koidz*, *Taraxacum hondoense Nakai*, *Taraxacum platycarpum* Dahls, *Taraxacum japonicum*, *Taraxacum officinale* Weber, and *Taraxacum kok-saghyz*; the genus *Ficus*, e.g., *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis*; the genus *Parthenium*, e.g., *Parthenium argentatum*, *Parthenium hysterophores*, and annual ragweed (*Ambrosia artemisiifolia*); and lettuce (*Lactuca sativa*).

Specific examples of the CPT family protein found on rubber particles include HRT1 and HRT2 which are CPT family proteins found on rubber particles derived from *Hevea brasiliensis*, CPT1 which is a CPT family protein found on rubber particles derived from *Taraxacum kok-saghyz*, and CPT3 which is a CPT family protein found on rubber particles derived from *Parthenium argentatum*. HRT1 is preferred among these.

A specific example of the CPT family protein found on rubber particles is the following protein [1]:

[1] a protein having the amino acid sequence represented by SEQ ID NO:1.

It is also known that proteins having one or more amino acid substitutions, deletions, insertions, or additions relative to the original amino acid sequence can still have the inherent function. Thus, another specific example of the CPT family protein is the following protein [2]:

[2] a protein having an amino acid sequence containing one or more amino acid substitutions, deletions, insertions, and/or additions relative to the amino acid sequence represented by SEQ ID NO:1, and having an enzyme activity that catalyzes a reaction of cis-chain elongation of an isoprenoid compound.

Here, in order to maintain the function of the CPT family protein, it preferably has an amino acid sequence containing one or more, more preferably 1 to 58, still more preferably 1 to 44, further preferably 1 to 29, particularly preferably 1 to 15, most preferably 1 to 6, even most preferably 1 to 3 amino acid substitutions, deletions, insertions, and/or additions relative to the amino acid sequence of SEQ ID NO:1.

Conservative substitutions are preferred as examples of amino acid substitutions. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the CPT family protein is the following protein [3]:

[3] a protein having an amino acid sequence with at least 80% sequence identity to the amino acid sequence represented by SEQ ID NO:1, and having an enzyme activity that catalyzes a reaction of cis-chain elongation of an isoprenoid compound.

Here, in order to maintain the function of the CPT family protein, the sequence identity to the amino acid sequence of SEQ ID NO:1 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993), which is herein incorporated by reference] developed by Karlin and Altschul or FASTA [Methods Enzymol., 183, 63 (1990), which is herein incorporated by reference].

Whether it is a protein having the above enzyme activity may be determined by, for example, conventional techniques, such as by expressing a target protein in a transformant produced by introducing a gene coding for the target protein into Escherichia coli or other host organisms, and determining the presence or absence of the function of the target protein by the corresponding activity measuring method.

Specific examples of the gene coding for the CPT family protein found on rubber particles include the following DNAs [1] and [2]:

[1] a DNA having the nucleotide sequence represented by SEQ ID NO:2; and

[2] a DNA which hybridizes under stringent conditions to a DNA having a nucleotide sequence complementary to the nucleotide sequence represented by SEQ ID NO:2, and which codes for a protein having an enzyme activity that catalyzes a reaction of cis-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), each of which is herein incorporated by reference, and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be employed. Changes in stringency may be accomplished through the manipulation of formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the addition or substitution of blocking reagents used to suppress background in hybridization experiments. The addition of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence of SEQ ID NO:2 as calculated using a program such as BLAST or FASTA with the parameters mentioned above.

Whether the DNA which hybridizes to the above-mentioned DNA under stringent conditions codes for a protein having a predetermined enzyme activity may be determined by conventional techniques, such as by expressing a target protein in a transformant produced by introducing a gene coding for the target protein into Escherichia coli or other host organisms, and determining the presence or absence of the function of the target protein by the corresponding activity measuring method.

Moreover, conventional techniques may be employed to identify the amino acid sequence and nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence and amino acid sequence are identified by the RACE method, for example. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence or amino acid sequence can be identified by designing a primer containing a start codon and a primer containing a stop codon using the known nucleotide sequence, followed by performing RT-PCR using a synthesized cDNA as a template.

<<Cis-Prenyltransferase (CPT) Family Protein not Found on Rubber Particles>>

The cis-prenyltransferase (CPT) family protein not found on rubber particles may be any CPT family protein not found on rubber particles and may be, for example, a cis-prenyltransferase (CPT) family protein not found on rubber particles of plant origin. Here, examples of the plant include those mentioned above. In particular, the cis-prenyltransferase (CPT) family protein not found on rubber particles is preferably a cis-prenyltransferase (CPT) family protein not found on rubber particles derived from a plant of the genus *Hevea* or *Taraxacum* (particularly a plant of the genus *Hevea*), more preferably a cis-prenyltransferase (CPT) family protein not found on rubber particles derived from *Hevea brasiliensis* or *Taraxacum kok-saghyz* (particularly *Hevea brasiliensis*). It is also preferably a cis-prenyltransferase (CPT) family protein not found on rubber particles derived from *Arabidopsis thaliana*.

Specific examples of the CPT family protein not found on rubber particles include AtCPT4 and AtCPT5 which are CPTs not found on rubber particles derived from *Arabidopsis thaliana*, HbCPT4 and HbCPT5 which are CPTs not found on rubber particles derived from *Hevea brasiliensis*, and NDPS1 which is a CPT not found on rubber particles derived from *Solanum lycopersicum*. AtCPT5 or HbCPT5 is preferred among these.

Specific examples of the CPT family protein not found on rubber particles include the following protein [4]:
[4] a protein having the amino acid sequence represented by SEQ ID NO:3.

It is also known that proteins having one or more amino acid substitutions, deletions, insertions, or additions relative to the original amino acid sequence can still have the inherent function. Thus, another specific example of the CPT family protein is the following protein [5]:
[5] a protein having an amino acid sequence containing one or more amino acid substitutions, deletions, insertions, and/or additions relative to the amino acid sequence represented by SEQ ID NO:3, and having an enzyme activity that catalyzes a reaction of cis-chain elongation of an isoprenoid compound.

Here, in order to maintain the function of the CPT family protein, it preferably has an amino acid sequence containing one or more, more preferably 1 to 60, still more preferably 1 to 45, further preferably 1 to 30, particularly preferably 1 to 15, most preferably 1 to 6, even most preferably 1 to 3 amino acid substitutions, deletions, insertions, and/or additions relative to the amino acid sequence of SEQ ID NO:3.

Conservative substitutions are preferred as examples of amino acid substitutions. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the CPT family protein is the following protein [6]:
[6] a protein having an amino acid sequence with at least 80% sequence identity to the amino acid sequence represented by SEQ ID NO:3, and having an enzyme activity that catalyzes a reaction of cis-chain elongation of an isoprenoid compound.

Here, in order to maintain the function of the CPT family protein, the sequence identity to the amino acid sequence of SEQ ID NO:3 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993), which is herein incorporated by reference] developed by Karlin and Altschul or FASTA [Methods Enzymol., 183, 63 (1990), which is herein incorporated by reference].

Whether it is a protein having the above enzyme activity may be determined by, for example, conventional techniques, such as by expressing a target protein in a transformant produced by introducing a gene coding for the target protein into *Escherichia coli* or other host organisms, and determining the presence or absence of the function of the target protein by the corresponding activity measuring method.

Other specific examples of the CPT family protein not found on rubber particles include the following protein [7]:
[7] a protein having the amino acid sequence represented by SEQ ID NO:4.

It is also known that proteins having one or more amino acid substitutions, deletions, insertions, or additions relative to the original amino acid sequence can still have the inherent function. Thus, another specific examples of the CPT family protein is the following protein [8]:
[8] a protein having an amino acid sequence containing one or more amino acid substitutions, deletions, insertions, and/or additions relative to the amino acid sequence represented by SEQ ID NO:4, and having an enzyme activity that catalyzes a reaction of cis-chain elongation of an isoprenoid compound.

Here, in order to maintain the function of the CPT family protein, it preferably has an amino acid sequence containing one or more, more preferably 1 to 73, still more preferably 1 to 55, further preferably 1 to 37, particularly preferably 1 to 18, most preferably 1 to 7, even most preferably 1 to 4 amino acid substitutions, deletions, insertions, and/or additions relative to the amino acid sequence of SEQ ID NO:4.

Conservative substitutions are preferred as examples of amino acid substitutions. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the CPT family protein is the following protein [9]:
[9] a protein having an amino acid sequence with at least 80% sequence identity to the amino acid sequence represented by SEQ ID NO:4, and having an enzyme activity that catalyzes a reaction of cis-chain elongation of an isoprenoid compound.

Here, in order to maintain the function of the CPT family protein, the sequence identity to the amino acid sequence of SEQ ID NO:4 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993), which is herein incorporated by reference] developed by Karlin and Altschul or FASTA [Methods Enzymol., 183, 63 (1990), which is herein incorporated by reference].

Whether it is a protein having the above enzyme activity may be determined by, for example, conventional techniques, such as by expressing a target protein in a transformant produced by introducing a gene coding for the target protein into *Escherichia coli* or other host organisms, and determining the presence or absence of the function of the target protein by the corresponding activity measuring method.

Specific examples of the gene coding for the CPT family protein not found on rubber particles include the following DNAs [3] and [4]:

[3] a DNA having the nucleotide sequence represented by SEQ ID NO:5; and

[4] a DNA which hybridizes under stringent conditions to a DNA having a nucleotide sequence complementary to the nucleotide sequence represented by SEQ ID NO:5, and which codes for a protein having an enzyme activity that catalyzes a reaction of cis-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), each of which is herein incorporated by reference, and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/L denatured salmon sperm DNA, followed by washing the filter for example in a 0.2×SSC solution at approximately 65° C. Less stringent conditions may also be employed. Changes in stringency may be accomplished through the manipulation of formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 µg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the addition or substitution of blocking reagents used to suppress background in hybridization experiments. The addition of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence of SEQ ID NO:5 as calculated using a program such as BLAST or FASTA with the parameters mentioned above.

Whether the DNA which hybridizes to the above-mentioned DNA under stringent conditions codes for a protein having a predetermined enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Moreover, conventional techniques may be employed to identify the amino acid sequence and nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence and amino acid sequence are identified by the RACE method, for example. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence and amino acid sequence can be identified by designing a primer containing a start codon and a primer containing a stop codon using the known nucleotide sequence, followed by performing RT-PCR using a synthesized cDNA as a template.

Other specific examples of the gene coding for the CPT family protein not found on rubber particles include the following DNAs [5] and [6]:

[5] a DNA having the nucleotide sequence represented by SEQ ID NO:6; and

[6] a DNA which hybridizes under stringent conditions to a DNA having a nucleotide sequence complementary to the nucleotide sequence represented by SEQ ID NO:6, and which codes for a protein having an enzyme activity that catalyzes a reaction of cis-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), each of which is herein incorporated by reference, and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be employed. Changes in stringency may be accomplished through the manipulation of formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the addition or substitution of blocking reagents used to suppress background in hybridization experiments. The addition of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence of SEQ ID NO:6 as calculated using a program such as BLAST or FASTA with the parameters mentioned above.

Whether the DNA which hybridizes to the above-mentioned DNA under stringent conditions codes for a protein having a predetermined enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Moreover, conventional techniques may be employed to identify the amino acid sequence and nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence and amino acid sequence are identified by the RACE method, for example. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence and amino acid sequence can be identified by designing a primer containing a start codon and a primer containing a stop codon using the known nucleotide sequence, followed by performing RT-PCR using a synthesized cDNA as a template.

<<Specific Examples of Mutant Cis-Prenyltransferase (CPT) Family Protein>>

Specific examples of the mutant CPT family protein include the following protein [A-1]:

[A-1] a protein having the amino acid sequence represented by SEQ ID NO:7.

It is also known that proteins having one or more amino acid substitutions, deletions, insertions, or additions relative to the original amino acid sequence can still have the inherent function. Thus, another specific example of the mutant CPT family protein is the following protein [A-2]:

[A-2] a protein having an amino acid sequence containing one or more amino acid substitutions, deletions, insertions, and/or additions relative to the amino acid sequence represented by SEQ ID NO:7, and having an enzyme activity that catalyzes a reaction of cis-chain elongation of an isoprenoid compound.

Here, in order to maintain the function of the mutant CPT family protein, it preferably has an amino acid sequence containing one or more, more preferably 1 to 61, still more preferably 1 to 46, further preferably 1 to 31, particularly preferably 1 to 15, most preferably 1 to 6, even most preferably 1 to 3 amino acid substitutions, deletions, insertions, and/or additions relative to the amino acid sequence of SEQ ID NO:7.

Conservative substitutions are preferred as examples of amino acid substitutions. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the mutant CPT family protein is the following protein [A-3]:

[A-3] a protein having an amino acid sequence with at least 80% sequence identity to the amino acid sequence represented by SEQ ID NO:7, and having an enzyme activity that catalyzes a reaction of cis-chain elongation of an isoprenoid compound.

Here, in order to maintain the function of the mutant CPT family protein, the sequence identity to the amino acid sequence of SEQ ID NO:7 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993), which is herein incorporated by reference] developed by Karlin and Altschul or FASTA [Methods Enzymol., 183, 63 (1990), which is herein incorporated by reference].

Whether it is a protein having the above enzyme activity may be determined by, for examples, conventional techniques, such as by expressing a target protein in a transformant produced by introducing a gene coding for the target protein into *Escherichia coli* or other host organisms, and determining the presence or absence of the function of the target protein by the corresponding activity measuring method.

Other specific examples of the mutant CPT family protein include the following protein [B-1]:

[B-1] a protein having the amino acid sequence represented by SEQ ID NO:8.

It is also known that proteins having one or more amino acid substitutions, deletions, insertions, or additions relative to the original amino acid sequence can still have the inherent function. Thus, another specific example of the mutant CPT family protein is the following protein [B-2]:

[B-2] a protein having an amino acid sequence containing one or more amino acid substitutions, deletions, insertions, and/or additions relative to the amino acid sequence represented by SEQ ID NO:8, and having an enzyme activity that catalyzes a reaction of cis-chain elongation of an isoprenoid compound.

Here, in order to maintain the function of the mutant CPT family protein, it preferably has an amino acid sequence containing one or more, more preferably 1 to 74, still more preferably 1 to 55, further preferably 1 to 37, particularly preferably 1 to 18, most preferably 1 to 7, even most preferably 1 to 4 amino acid substitutions, deletions, insertions, and/or additions relative to the amino acid sequence of SEQ ID NO:8.

Conservative substitutions are preferred as examples of amino acid substitutions. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the mutant CPT family protein is the following protein [B-3]:

[B-3] a protein having an amino acid sequence with at least 80% sequence identity to the amino acid sequence represented by SEQ ID NO:8, and having an enzyme activity that catalyzes a reaction of cis-chain elongation of an isoprenoid compound.

Here, in order to maintain the function of the mutant CPT family protein, the sequence identity to the amino acid sequence of SEQ ID NO:8 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993), which is herein incorporated by reference] developed by Karlin and Altschul or FASTA [Methods Enzymol., 183, 63 (1990), which is herein incorporated by reference].

Whether it is a protein having the above enzyme activity may be determined by, for example, conventional techniques, such as by expressing a target protein in a transformant produced by introducing a gene coding for the target protein into *Escherichia coli* or other host organisms, and determining the presence or absence of the function of the target protein by the corresponding activity measuring method.

Specific examples of the gene coding for the mutant CPT family protein include the following DNAs [C-1] and [C-2]:

[C-1] a DNA having the nucleotide sequence represented by SEQ ID NO:9; and

[C-2] a DNA which hybridizes under stringent conditions to a DNA having a nucleotide sequence complementary to the nucleotide sequence represented by SEQ ID NO:9, and which codes for a protein having an enzyme activity that catalyzes a reaction of cis-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), each of which is herein incorporated by reference, and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be employed. Changes in stringency may be accomplished through the manipulation of formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the addition or substitution of blocking reagents used to suppress background in hybridization experiments. The addition of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence of SEQ ID NO:9 as calculated using a program such as BLAST or FASTA with the parameters mentioned above.

Whether the DNA which hybridizes to the above-mentioned DNA under stringent conditions codes for a protein having a predetermined enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Moreover, conventional techniques may be employed to identify the amino acid sequence and nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence and amino acid sequence are identified by the RACE method, for example. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence and amino acid sequence can be identified by designing a primer containing a start codon and a primer containing a stop codon using the known nucleotide sequence, followed by performing RT-PCR using a synthesized cDNA as a template.

Specific examples of the gene coding for the mutant CPT family protein include the following DNAs [D-1] and [D-2]:
[D-1] a DNA having the nucleotide sequence represented by SEQ ID NO:10; and
[D-2] a DNA which hybridizes under stringent conditions to a DNA having a nucleotide sequence complementary to the nucleotide sequence represented by SEQ ID NO:10, and which codes for a protein having an enzyme activity that catalyzes a reaction of cis-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), each of which is herein incorporated by reference, and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be employed. Changes in stringency may be accomplished through the manipulation of formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the addition or substitution of blocking reagents used to suppress background in hybridization experiments. The addition of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence of SEQ ID NO:10 as calculated using a program such as BLAST or FASTA with the parameters mentioned above.

Whether the DNA which hybridizes to the above-mentioned DNA under stringent conditions codes for a protein having a predetermined enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Moreover, conventional techniques may be employed to identify the amino acid sequence and nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence and amino acid sequence are identified by the RACE method, for example. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence and amino acid sequence can be identified by designing a primer containing a start codon and a primer containing a stop codon using the known nucleotide sequence, followed by performing RT-PCR using a synthesized cDNA as a template.

<Method for Producing Polyisoprenoid>

The method for producing a polyisoprenoid of the present disclosure is characterized by using the mutant cis-prenyltransferase (CPT) family protein of the present disclosure.

The method for producing a polyisoprenoid of the present disclosure may be any method using the mutant CPT family protein of the present disclosure. The method preferably includes binding the mutant CPT family protein of the present disclosure to membrane particles (preferably rubber particles) in vitro. Binding the mutant CPT family protein to membrane particles (preferably rubber particles) in vitro permits the synthesis of a polyisoprenoid in the membrane particles (preferably rubber particles), which enables the production of a higher molecular weight polyisoprenoid. This is because the produced polyisoprenoid will accumulate inside the membrane particles (preferably rubber particles), which enables the formation of a product having a longer chain length than that produced when the protein is not bound to membrane particles (preferably rubber particles).

Herein, the term "polyisoprenoid" is a collective term for polymers composed of isoprene units ($C_5H_8$), specifically natural products including a cis-1,4-polyisoprene or trans-1,4-polyisoprene as the basic carbon skeleton. Examples of the polyisoprenoid include polymers such as solanesol ($C_{45}$), undecaprenyl phosphate ($C_{55}$), gutta percha, and rubber. The polyisoprenoid is preferably a cis-polyisoprenoid in which isoprene units are bound in a cis configuration. Moreover, herein, the term "isoprenoid" refers to a compound containing an isoprene unit ($C_5H_8$) and conceptually includes polyisoprenoids.

The membrane particles may be any particle having a membrane structure. Examples include biomembranes such as rubber particles and lipid droplets, and artificial membranes such as nanodiscs and liposomes. These may be used alone or in combinations of two or more. Rubber particles are preferred among these. The description below will discuss embodiments in which the membrane particles are rubber particles. The same may apply to other membrane particles.

Here, the production method of the present disclosure may include steps other than the binding step, and each step may be performed once or repeated multiple times.

Moreover, the amount of the mutant CPT family protein to be bound to the rubber particles is not limited.

Herein, the expression "the mutant CPT family protein binds to rubber particles" means, for example, that the mutant CPT family protein is fully or partially incorporated into the rubber particles or fully or partially inserted into the membrane structure of the rubber particles. It is not limited to these embodiments and also means embodiments in which the protein is localized on the surface or inside of the rubber particles. Moreover, the concept of binding to rubber particles also includes embodiments in which the mutant CPT family protein forms a complex with a protein bound to the rubber particles to be present in the form of the complex on the rubber particles. The same may apply to other membrane particles.

The origin of the rubber particles is not limited. For example, the rubber particles may be derived from the latex of a rubber-producing plant such as *Hevea brasiliensis, Taraxacum kok-saghyz, Parthenium argentatum*, or *Sonchus oleraceus*.

The particle size of the rubber particles is also not limited. Rubber particles having a predetermined particle size may be sorted out and used, or a mixture of rubber particles having different particle sizes may be used. Even when rubber particles having a predetermined particle size are sorted out and used, the rubber particles used may be either small rubber particles (SRP) having a small particle size or large rubber particles (LRP) having a large particle size.

Commonly used methods may be employed for sorting out the rubber particles having a predetermined particle size, including, for example, methods which involve centrifugation, preferably multistage centrifugation. An exemplary specific method includes centrifugation at 500-1500×g, centrifugation at 1700-2500×g, centrifugation at 7000-9000×g, centrifugation at 15000-25000×g, and centrifugation at 40000-60000×g, carried out in said order. Here, the duration of each centrifugation is preferably 20 minutes or longer, more preferably 30 minutes or longer, still more preferably 40 minutes or longer, but is preferably 120 minutes or shorter, more preferably 90 minutes or shorter. Moreover, the temperature for each centrifugation is preferably 0 to 10° C., more preferably 2 to 8° C., particularly preferably 4° C.

In the binding step, a protein expressed from a gene coding for the mutant CPT family protein is bound to rubber particles in vitro.

The gene coding for the mutant CPT family protein is as described above.

Moreover, as the mutant CPT family protein is obtained by mutating the amino acid sequence of a C-terminal region of a CPT family protein not found on rubber particles to be identical or similar to the amino acid sequence of a C-terminal region of a CPT family protein found on rubber particles, when the origin of the CPT family protein found on rubber particles is the same as the origin of the rubber particles to be bound to the mutant CPT family protein, the origin of the amino acid sequence of the C-terminal region of the mutant CPT family protein is the same as the origin of the rubber particles to be bound to the mutant CPT family protein, so that the binding ability between the mutant CPT family protein and the rubber particles can be further enhanced.

For example, when rubber particles derived from *Hevea brasiliensis* are used, the mutant protein used is preferably the mutant CPT family protein in which the C-terminal region is substituted by a C-terminal region of a CPT family protein found on rubber particles derived from *Hevea brasiliensis* (HRT1). Or, when rubber particles derived from *Taraxacum kok-saghyz* are used, the mutant protein used is preferably the mutant CPT family protein in which the C-terminal region is substituted by a C-terminal region of a CPT family protein found on rubber particles derived from *Taraxacum kok-saghyz*.

Here, in the binding step, as long as the protein expressed from the gene coding for the mutant CPT family protein is bound to rubber particles in vitro, one or more additional proteins may also be bound thereto.

The origin of the additional proteins is not limited, but the additional proteins are preferably derived from a plant, more preferably a rubber-producing plant, still more preferably at least one selected from the group consisting of plants of the genera *Hevea, Sonchus, Taraxacum,* and *Parthenium.* In particular, they are further preferably derived from at least one plant selected from the group consisting of *Hevea brasiliensis, Sonchus oleraceus, Parthenium argentatum,* and *Taraxacum kok-saghyz,* particularly preferably from *Hevea brasiliensis.*

The additional proteins are not limited and may be any protein, but in view of the rubber synthesis ability of the rubber particles, they are each preferably a protein that is naturally found on rubber particles in a rubber-producing plant. Here, the protein found on rubber particles may be a protein that binds to a large part of the membrane surface of rubber particles, or a protein that binds to the membrane of rubber particles so as to be inserted thereinto, or a protein that forms a complex with a protein bound to the membrane to be present on the membrane surface.

Examples of the protein that is naturally found on rubber particles in a rubber-producing plant include HRT1-REF-bridging protein (HRBP), rubber elongation factor (REF), small rubber particle protein (SRPP), β-1,3-glucanase, and Hevein. HRT1-REF-bridging protein (HRBP) or rubber elongation factor (REF) is preferred among these.

The binding step may be carried out using any means that can bind the mutant CPT family protein to rubber particles in vitro, such as, for example, by performing protein synthesis in the presence of both rubber particles and a cell-free protein synthesis solution containing an mRNA coding for the mutant CPT family protein to bind the mutant CPT family protein to the rubber particles.

The binding step preferably includes performing protein synthesis in the presence of both rubber particles and a cell-free protein synthesis solution containing an mRNA coding for the mutant CPT family protein to bind the mutant CPT family protein to the rubber particles, among other methods.

In other words, it is preferred to obtain rubber particles bound to the mutant CPT family protein by performing protein synthesis in the presence of both rubber particles and a cell-free protein synthesis solution containing an mRNA coding for the mutant CPT family protein, or, more specifically, using a mixture of rubber particles with a cell-free protein synthesis solution containing an mRNA coding for the mutant CPT family protein.

The protein synthesis performed in the presence of both rubber particles and a cell-free protein synthesis solution containing an mRNA coding for the mutant CPT family protein is namely the synthesis of the mutant CPT family protein by cell-free protein synthesis, which can synthesize the mutant CPT family protein maintaining its biological function (native state). The cell-free protein synthesis performed in the presence of rubber particles allows the synthesized mutant CPT family protein in the native state to bind to the rubber particles.

Here, the expression "performing protein synthesis in the presence of both the cell-free protein synthesis solution and rubber particles to bind the mutant CPT family protein to the rubber particles" means, for example, that each mutant CPT family protein synthesized by the protein synthesis is fully or partially incorporated into the rubber particles or fully or partially inserted into the membrane structure of the rubber particles. It is not limited to these embodiments and also means embodiments in which, for example, the protein is localized on the surface or inside of the rubber particles. Moreover, the concept of binding to rubber particles also includes embodiments in which the protein forms a complex with a protein bound to the rubber particles as described above to be present in the form of the complex on the rubber particles.

Each mRNA coding for the mutant CPT family protein serves as a translation template that can be translated to synthesize the mutant CPT family protein.

Each mRNA coding for the mutant CPT family protein may be prepared by any method as long as the prepared mRNA serves as a translation template that can be translated to synthesize the mutant CPT family protein.

As long as the cell-free protein synthesis solution contains the mRNA coding for the mutant CPT family protein, it may contain an mRNA coding for an additional protein.

The mRNA coding for an additional protein may be one that can be translated to express the additional protein. Here, the additional protein may be as described above.

In the binding step, cell-free protein synthesis of the mutant CPT family protein is preferably performed in the presence of rubber particles. This cell-free protein synthesis may be carried out using the cell-free protein synthesis solution in a similar manner to conventional methods. The cell-free protein synthesis system used may be a common cell-free protein synthesis means, examples of which include rapid translation system RTS500 (Roche Diagnostics); and wheat germ extracts prepared in accordance with Proc. Natl. Acad. Sci. USA, 97:559-564 (2000), JP 2000-236896 A, JP 2002-125693 A, and JP 2002-204689 A, each of which is herein incorporated by reference, or their cell-free protein synthesis systems (JP 2002-204689 A, Proc. Natl. Acad. Sci. USA, 99:14652-14657 (2002), each of which is herein incorporated by reference). Systems using germ extracts are preferred among these.

The source of the germ extracts is not limited. From the standpoint of translation efficiency, it is preferred to use a plant-derived germ extract for cell-free protein synthesis of a plant protein. It is particularly preferred to use a wheat-derived germ extract.

The method for preparing such a germ extract is not limited, and may be carried out conventionally, as described in, for example, JP 2005-218357 A, which is herein incorporated by reference.

The cell-free protein synthesis solution preferably further contains a cyclic nucleoside monophosphate derivative or a salt thereof (hereinafter, also referred to simply as "activity enhancer"). Protein synthesis activity can be further enhanced by the inclusion of the activity enhancer.

The cyclic nucleoside monophosphate derivative or salt thereof is not limited as long as it can enhance cell-free protein synthesis activity. Examples include adenosine-3', 5'-cyclic monophosphoric acid and its salts; adenosine-3', 5'-cyclic monophosphorothioic acid (Sp-isomer) and its salts; adenosine-3', 5'-cyclic monophosphorothioic acid (Rp-isomer) and its salts; guanosine-3', 5'-cyclic monophosphoric acid and its salts; guanosine-3', 5'-cyclic monophosphorothioic acid (Sp-isomer) and its salts; guanosine-3', 5'-cyclic monophosphorothioic acid (Rp-isomer) and its salts; 8-bromoadenosine-3', 5'-cyclic monophosphoric acid (bromo-cAMP) and its salts; 8-(4-chlorophenylthio)adenosine-3', 5'-cyclic monophosphoric acid (chlorophenylthio-cAMP) and its salts; 5,6-dichloro-1-β-D-ribofuranosylbenzimidazole adenosine-3', 5'-cyclic monophosphoric acid (dichlororibofuranosylbenzimidazole cAMP) and its salts; adenosine-2', 5'-cyclic monophosphoric acid and its salts; adenosine-2', 5'-cyclic monophosphorothioic acid (Sp-isomer) and its salts; adenosine-2', 5'-cyclic monophosphoro-thioic acid (Rp-isomer) and its salts; guanosine-2', 5'-cyclic monophosphoric acid and its salts; guanosine-2', 5'-cyclic monophosphorothioic acid (Sp-isomer) and its salts; and guanosine-2', 5'-cyclic monophosphorothioic acid (Rp-isomer) and its salts.

The base that forms a salt with the cyclic nucleoside monophosphate derivative is not limited as long as it is biochemically acceptable and forms a salt with the derivative. Preferred are, for example, alkali metal atoms such as sodium or potassium, and organic bases such as tris-hydroxyaminomethane, among others.

Among these activity enhancers, adenosine-3', 5'-cyclic monophosphoric acid or adenosine-3', 5'-cyclic monophosphate sodium salt is particularly preferred. Moreover, these activity enhancers may be used alone or in combinations of two or more.

The activity enhancer may be added to the cell-free protein synthesis solution in advance, but if the activity enhancer is unstable in the solution, it is preferably added during the protein synthesis reaction performed in the presence of both the cell-free protein synthesis solution and rubber particles.

The amount of the activity enhancer(s) added is not limited as long as it is at a concentration that can activate (increase) the protein synthesis reaction in the cell-free protein synthesis solution. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

The temperature of the cell-free protein synthesis solution at which the activity enhancer is added to the cell-free protein synthesis solution is not limited, but is preferably 0 to 30° C., more preferably 10 to 26° C.

In addition to the mRNA (translation template) coding for the mutant CPT family protein, the cell-free protein synthesis solution also contains ATP, GTP, creatine phosphate, creatine kinase, L-amino acids, potassium ions, magnesium ions, and other components required for protein synthesis, and optionally an activity enhancer. The use of such a cell-free protein synthesis solution can provide a cell-free protein synthesis reaction system.

Here, since the germ extract prepared as described in JP 2005-218357 A above contains tRNA in an amount necessary for protein synthesis reaction, addition of separately prepared tRNA is not required when the germ extract prepared as above is used in the cell-free protein synthesis solution. In other words, tRNA may be added to the cell-free protein synthesis solution, if necessary.

The binding step preferably includes performing protein synthesis in the presence of both rubber particles and a cell-free protein synthesis solution containing an mRNA coding for the mutant CPT family protein. Specifically, this can be accomplished by adding rubber particles to the cell-free protein synthesis solution at a suitable time either before or after the protein synthesis, preferably before the protein synthesis.

Moreover, the concentration of rubber particles present with the cell-free protein synthesis solution is preferably 5 to 50 g/L. In other words, 5 to 50 g of rubber particles are preferably present in 1 L of the cell-free protein synthesis solution. If the concentration of rubber particles present with the cell-free protein synthesis solution is less than 5 g/L, a rubber layer may not be formed by separation treatment (e.g., ultracentrifugation) for collecting the rubber particles bound to the synthesized mutant CPT family protein, and therefore it may be difficult to collect the rubber particles bound to the synthesized mutant CPT family protein. Moreover, if the concentration of rubber particles present with the cell-free protein synthesis solution exceeds 50 g/L, the rubber particles may aggregate, so that the synthesized mutant CPT family protein may fail to bind well to the rubber particles. The concentration of rubber particles is more preferably 10 to 40 g/L, still more preferably 15 to 35 g/L, particularly preferably 15 to 30 g/L.

Moreover, in the protein synthesis in the presence of both rubber particles and the cell-free protein synthesis solution, additional rubber particles may be appropriately added as the reaction progresses. The cell-free protein synthesis solution and rubber particles are preferably allowed to be present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g., pretreatment, before use in the binding step, preferably before being combined with the cell-free protein synthesis solution. However, the proteins present on the rubber particles may be removed to some extent from the rubber particles with a surfactant beforehand to increase the proportion of the mutant CPT family protein desired to be bound. Then, the rubber particles after the removal preferably have a residual rubber synthesis activity that is at least 50% of that before the removal.

The surfactant is not limited, and examples include nonionic surfactants and amphoteric surfactants. Nonionic or amphoteric surfactants, among others, are suitable because they have only a little denaturing effect on the proteins on the membrane, and amphoteric surfactants are especially suitable. Thus, in another suitable embodiment of the first disclosure, the surfactant is an amphoteric surfactant.

These surfactants may be used alone or in combinations of two or more.

Examples of the nonionic surfactants include polyoxyalkylene ether nonionic surfactants, polyoxyalkylene ester nonionic surfactants, polyhydric alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Polyoxyalkylene ether or polyhydric alcohol fatty acid ester nonionic surfactants are preferred among these.

Examples of the polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyrylphenyl ethers. Among these, polyoxyalkylene alkylphenyl ethers are suitable. Here, the polyol is preferably a C2-C12 polyhydric alcohol, such as ethylene glycol, propylene glycol, glycerin, sorbitol, glucose, sucrose, pentaerythritol, or sorbitan.

Examples of the polyoxyalkylene ester nonionic surfactants include polyoxyalkylene fatty acid esters and polyoxyalkylene alkyl rosin acid esters.

Examples of the polyhydric alcohol fatty acid ester nonionic surfactants include fatty acid esters of C2-C12 polyhydric alcohols and fatty acid esters of polyoxyalkylene polyhydric alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing such as polyoxyalkylene sorbitan fatty acid esters and polyoxyalkylene glycerin fatty acid esters. Among these, sorbitan fatty acid esters are suitable.

Examples of the sugar fatty acid ester nonionic surfactants include fatty acid esters of sucrose, glucose, maltose, fructose, and polysaccharides, as well as polyalkylene oxide adducts of the foregoing.

Examples of the alkyl polyglycoside nonionic surfactants include those having, for example, glucose, maltose, fructose, or sucrose as the glycoside, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include C4-C30 linear or branched, saturated or unsaturated alkyl groups. Moreover, the polyoxyalkylene groups may have C2-C4 alkylene groups, and may have about 1 to 50 moles of added ethylene oxide, for example. Moreover, examples of the fatty acids include C4-C30 linear or branched, saturated or unsaturated fatty acids.

Among the nonionic surfactants, polyoxyethyleneethylene (10) octylphenyl ether (Triton X-100) or sorbitan monolaurate (Span 20) is particularly preferred for their ability to moderately remove membrane-associated proteins while keeping the membrane of rubber particles stable and, further, having only a little denaturing effect on proteins.

Examples of the amphoteric surfactants include zwitterionic surfactants such as quaternary ammonium base group/sulfonic acid group (—SO$_3$H) surfactants, (water-soluble) quaternary ammonium base group/phosphoric acid group surfactants, (water-insoluble) quaternary ammonium base group/phosphoric acid group surfactants, and quaternary ammonium base group/carboxyl group surfactants. Here, the acid groups may be salts.

In particular, such a zwitterionic surfactant preferably has both positive and negative charges in a molecule, and the acid dissociation constant (pKa) of the acid group is preferably 5 or less, more preferably 4 or less, still more preferably 3 or less.

Specific examples of the amphoteric surfactants include ammonium sulfobetaines such as 3-[(3-cholamidopropyl) dimethylammonio]-2-hydroxy-1-propanesulfonate (CHAPSO), 3-[(3-cholamidopropyl)-dimethylammonio]-propanesulfonate (CHAPS), N,N-bis(3-D-gluconamidopropyl)-cholamide, n-octadecyl-N,N'-dimethyl-3-ammonio-1-propanesulfonate, n-decyl-N,N'-dimethyl-3-ammonio-1-propanesulfonate, n-dodecyl-N,N'-dimethyl-3-ammonio-1-propanesulfonate, n-tetradecyl-N,N'-dimethyl-3-ammonio-1-propanesulfonate (Zwittergent® 3-14), and n-hexadecyl-N,N'-dimethyl-3-ammonio-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Among these, 3-[(3-cholamidopropyl)dimethylammonio]-propanesulfonate (CHAPS) is particularly preferred for its ability to moderately remove proteins while keeping the membrane of rubber particles stable.

The surfactant concentration for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. Moreover, the lower limit is preferably at least 0.05 times, more preferably at least 0.1 times, still more preferably at least 0.3 times the CMC.

Examples of reaction systems or apparatuses for protein synthesis that may be used in the cell-free protein synthesis include a batch method (Pratt, J. M. et al., Transcription and Translation, Hames, 179-209, B. D. & Higgins, S. J., eds, IRL Press, Oxford (1984), which is herein incorporated by reference), a continuous cell-free protein synthesis system in which amino acids, energy sources, and other components are supplied continuously to the reaction system (Spirin, A. S. et al., Science, 242, 1162-1164 (1988), which is herein incorporated by reference), a dialysis method (Kigawa et al., 21st Annual Meeting of the Molecular Biology Society of Japan, WID 6, which is herein incorporated by reference), and an overlay method (instruction manual of PROTEIOS™ wheat germ cell-free protein synthesis core kit, Toyobo Co., Ltd., which is herein incorporated by reference). Other methods may include supplying template RNA, amino acids, energy sources, and other components, if necessary, to the protein synthesis reaction system, and discharging the synthesis product or decomposition product as required.

The dialysis method is preferred among these. The reason for this is as follows. The overlay method has the advantage of easy operation, but unfortunately rubber particles disperse in the reaction solution and thus are difficult to efficiently bind to the synthesized mutant CPT family protein. In contrast, in the dialysis method, since the amino acids used as the raw materials of the mutant CPT family protein to be synthesized can pass through the dialysis membrane while rubber particles cannot pass therethrough, it is possible to prevent dispersal of rubber particles and thus to efficiently bind the synthesized mutant CPT family protein to rubber particles.

Here, the dialysis method refers to a method in which protein synthesis is performed using an apparatus in which the synthesis reaction solution for protein synthesis used in the cell-free protein synthesis is used as an internal dialysis solution and is separated from an external dialysis solution by a dialysis membrane capable of mass transfer. Specifically, for example, the synthesis reaction solution excluding the translation template is optionally pre-incubated for an appropriate amount of time, to which is then added the translation template and the mixture is put in an appropriate dialysis container as the internal reaction solution. Examples of the dialysis container include containers with a dialysis membrane attached to the bottom (e.g., Dialysis Cup 12,000 available from Daiichi Kagaku) and dialysis tubes (e.g., 12,000 available from Sanko Junyaku Co., Ltd.). The dialysis membrane used may have a molecular weight cutoff of 10,000 daltons or more, preferably about 12,000 daltons.

The external dialysis solution used may be a buffer containing amino acids. Dialysis efficiency can be increased by replacing the external dialysis solution with a fresh one when the reaction speed declines. The reaction temperature and time may be selected appropriately according to the protein synthesis system used. For example, in the case of a system using a wheat-derived germ extract, the reaction may be carried out usually at 10 to 40° C., preferably 18 to 30°

C., more preferably 20 to 26° C., for 10 minutes to 48 hours, preferably for 10 minutes to 30 hours, more preferably for 10 minutes to 24 hours.

Moreover, since the mRNA coding for the mutant CPT family protein contained in the cell-free protein synthesis solution is easily broken down, the mRNA may be additionally added as appropriate during the protein synthesis reaction to make the protein synthesis more efficient. Here, the addition time, the number of additions, the addition amount, and other conditions of the mRNA are not limited and may be selected appropriately.

In the production method of the first disclosure, the step of binding a protein expressed from a gene coding for the mutant CPT family protein to rubber particles in vitro may optionally be followed by collecting the rubber particles.

The rubber particle collection step may be carried out by any method that can collect the rubber particles. It may be carried out by conventional methods for collecting rubber particles. Specific examples include methods using centrifugation. When the rubber particles are collected by the centrifugation methods, the centrifugal force, centrifugation time, and centrifugation temperature may be selected appropriately so as to be able to collect the rubber particles. For example, the centrifugal force during the centrifugation is preferably 15000×g or more, more preferably 20000×g or more, still more preferably 25000×g or more. However, since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. However, since increasing the centrifugation time too much is not expected to produce a correspondingly high separation effect, the upper limit of the centrifugation time is preferably 120 minutes or less, more preferably 90 minutes or less.

Moreover, from the standpoint of maintaining the activity of the mutant CPT family protein bound to rubber particles, the centrifugation temperature is preferably 0 to 10° C., more preferably 2 to 8° C., particularly preferably 4° C.

For example, when the cell-free protein synthesis is performed, the centrifugation may be performed to separate the rubber particles and the cell-free protein synthesis solution into the upper and lower layers, respectively. The cell-free protein synthesis solution as the lower layer may then be removed to collect the rubber particles bound to the mutant CPT family protein. The collected rubber particles may be re-suspended in an appropriate buffer having a neutral pH for storage.

Here, the rubber particles collected by the rubber particle collection step can be used in the same way as usual natural rubber without the need for further special treatment.

Further, the polyisoprenoid produced by the method for producing a polyisoprenoid of the first disclosure may be recovered by subjecting the rubber particles to the solidification step described below.

The solidification step may be carried out by any solidification method, such as by adding the rubber particles to a solvent that does not dissolve polyisoprenoids, such as ethanol, methanol, or acetone, or by adding an acid to the rubber particles. Rubber (a type of polyisoprenoid) can be recovered as solids from the rubber particles by the solidification step. The obtained rubber may be dried if necessary before use.

Thus, according to the first disclosure, by binding a protein expressed from a gene coding for the mutant CPT family protein to rubber particles in vitro, it is possible to synthesize a polyisoprenoid in the rubber particles, and therefore it is possible to efficiently produce a high molecular weight polyisoprenoid in a reaction vessel (e.g., a test tube or industrial plant).

(Method for Producing Rubber Product)

The method for producing a rubber product of the first disclosure includes: producing a polyisoprenoid by the method for producing a polyisoprenoid of the first disclosure; kneading the polyisoprenoid with an additive to obtain a kneaded mixture; forming a raw rubber product from the kneaded mixture; and vulcanizing the raw rubber product.

The rubber product may be any rubber product that can be produced from rubber, preferably natural rubber. Examples include pneumatic tires, rubber rollers, rubber fenders, gloves, and medical rubber tubes.

When the rubber product is a pneumatic tire, or in other words, when the method for producing a rubber product of the first disclosure is the method for producing a pneumatic tire of the first disclosure, the raw rubber product forming step corresponds to the step of building a green tire from the kneaded mixture, and the vulcanization step corresponds to the step of vulcanizing the green tire. Thus, the method for producing a pneumatic tire of the first disclosure includes: producing a polyisoprenoid by the method for producing a polyisoprenoid; kneading the polyisoprenoid with an additive to obtain a kneaded mixture; building a green tire from the kneaded mixture; and vulcanizing the green tire.

<Kneading Step>

In the kneading step, the polyisoprenoid produced by the method for producing a polyisoprenoid is kneaded with an additive to obtain a kneaded mixture.

Any additive may be used including those used in the production of rubber products. For example, when the rubber product is a pneumatic tire, examples of the additive include rubber components other than the polyisoprenoid, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

The kneading in the kneading step may be carried out using a rubber kneading machine such as an open roll mill, a Banbury mixer, or an internal mixer.

<Raw Rubber Product Forming Step (Green Tire Building Step in the Case of Tire)>

In the raw rubber product forming step, a raw rubber product (green tire in the case of tire) is formed from the kneaded mixture obtained in the kneading step.

The method for forming a raw rubber product is not limited, and methods used to form raw rubber products may be used appropriately. For example, when the rubber product is a pneumatic tire, the kneaded mixture obtained in the kneading step may be extruded into the shape of a tire component and then assembled with other tire components in a usual manner on a tire building machine to build a green tire (unvulcanized tire).

<Vulcanization Step>

In the vulcanization step, the raw rubber product obtained in the raw rubber product forming step is vulcanized to produce a rubber product.

The method for vulcanizing the raw rubber product is not limited, and methods used to vulcanize raw rubber products may be used appropriately. For example, when the rubber product is a pneumatic tire, the green tire (unvulcanized tire)

obtained in the raw rubber product forming step may be vulcanized by heating and pressing in a vulcanizer to produce a pneumatic tire.

(Second Disclosure)

(Vector)

The vector of the second disclosure contains a gene coding for the mutant cis-prenyltransferase (CPT) family protein of the present disclosure. When this vector is introduced into a plant for transformation, the gene coding for the mutant CPT family protein in the vector will be expressed to enable the production of a higher molecular weight polyisoprenoid in the plant as compared to before the gene recombination.

The vector preferably contains a promoter for use in protein expression in a plant and a gene coding for the mutant CPT family protein, functionally linked to the promoter. In this case, the gene coding for the mutant CPT family protein can be more suitably expressed in a plant.

Herein, the expression "a gene is functionally linked to a promoter" means that the gene sequence is linked downstream of the promoter so that it is controlled by the promoter.

The promoter for use in protein expression in a plant may be any one capable of functioning in plant cells. Examples include a cauliflower mosaic virus (CaMV) 35S promoter, a rice actin 1 promoter, a nopaline synthase gene promoter, a tobacco mosaic virus 35S promoter, a rice-derived actin gene promoter, and a ubiquitin promoter.

The vector more preferably contains a promoter having a promoter activity that drives laticifer-specific gene expression and a gene coding for the mutant CPT family protein, functionally linked to the promoter. When this vector is introduced into a plant for transformation, the gene coding for the mutant CPT family protein in the vector will be laticifer-specifically expressed to more suitably enable the production of a higher molecular weight polyisoprenoid in the plant as compared to before the gene recombination.

Herein, the expression "promoter has a promoter activity that drives laticifer-specific gene expression" means that the promoter has activity to control gene expression to cause a desired gene to be expressed specifically in laticifers when the desired gene is functionally linked to the promoter and introduced into a plant. Here, the term "laticifer-specific gene expression" means that the gene is expressed substantially exclusively in laticifers with no or little expression of the gene in the sites other than laticifers in a plant.

For example, the vector of the second disclosure can be prepared by inserting the nucleotide sequence of a promoter having a promoter activity that drives laticifer-specific gene expression and the nucleotide sequence of a gene coding for the mutant CPT family protein into a vector commonly known as a plant transformation vector by conventional techniques. Examples of vectors that can be used to prepare the vector of the second disclosure include pBI vectors, binary vectors such as pGA482, pGAH, and pBIG, intermediate plasmids such as pLGV23Neo, pNCAT, and pMON200, and pH35GS containing GATEWAY cassette.

As long as the vector of the second disclosure contains the nucleotide sequence of a gene coding for the mutant CPT family protein, it may contain additional nucleotide sequences in addition to the nucleotide sequence of a promoter. In addition to these nucleotide sequences, the vector usually contains vector-derived sequences as well as other sequences such as a restriction enzyme recognition sequence, a spacer sequence, a marker gene sequence, and a reporter gene sequence.

Examples of the marker gene include drug-resistant genes such as a kanamycin-resistant gene, a hygromycin-resistant gene, and a bleomycin-resistant gene. Moreover, the reporter gene is intended to be introduced to determine the expression site in a plant, and examples include a luciferase gene, a β-glucuronidase (GUS) gene, a green fluorescent protein (GFP), and a red fluorescent protein (RFP).

The gene coding for the mutant CPT family protein is as described above for the first disclosure.

The promoter having a promoter activity that drives laticifer-specific gene expression is preferably at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

Herein, the term "rubber elongation factor (REF)" refers to a rubber particle-associated protein that binds to rubber particles in the latex of rubber-producing plants such as *Hevea brasiliensis*, and contributes to stabilization of the rubber particles.

The term "small rubber particle protein (SRPP)" refers to a rubber particle-associated protein that binds to rubber particles in the latex of rubber-producing plants such as *Hevea brasiliensis*.

The term "Hevein 2.1 (HEV2.1)" refers to a protein that is highly expressed in the laticifer cells of rubber-producing plants such as *Hevea brasiliensis*. This protein is involved in coagulation of rubber particles and has antifungal activity.

Moreover, the term "MYC1 transcription factor (MYC1)" refers to a transcription factor that is highly expressed in the latex of rubber-producing plants such as *Hevea brasiliensis* and participates in jasmonic acid signaling. Here, the term "transcription factor" means a protein having activity to increase or decrease, preferably increase, gene transcription. In other words, MYC1 herein is a protein having activity (transcription factor activity) to increase or decrease, preferably increase, the transcription of a gene coding for at least one protein among the proteins involved in jasmonic acid signaling.

The vector of the second disclosure (which contains a gene coding for the mutant CPT family protein) may be introduced into a plant to produce a transgenic plant transformed to express the mutant CPT family protein involved in polyisoprenoid biosynthesis. Moreover, in the transgenic plant in which the mutant CPT family protein involved in polyisoprenoid biosynthesis is expressed, a certain function (e.g., enzyme activity) possessed by the protein is newly enhanced in the plant transfected with the vector of the second disclosure. As a result, the production of a higher molecular weight polyisoprenoid can be more suitably enabled in the plant as compared to before the gene recombination.

The method for preparing the transgenic plant is explained briefly below, though such a transgenic plant can be prepared by conventional methods.

The plant into which the vector of the second disclosure is to be introduced to produce the transgenic plant is not limited, but is preferably a rubber-producing plant, among others. This is because the production of a high molecular weight polyisoprenoid can be expected particularly when the mutant CPT family protein is expressed in a plant capable of biosynthesizing a polyisoprenoid. In particular, the plant is preferably a plant of the genus *Hevea* or *Taraxacum*, more preferably *Hevea brasiliensis* or *Taraxacum kok-saghyz*.

The vector of the second disclosure may be introduced into a plant (including plant cells, such as callus, cultured cells, spheroplasts, and protoplasts) by any method that can introduce DNA into plant cells. Examples include methods using *Agrobacterium* (JP S59-140885 A, JP S60-70080 A, WO94/00977, each of which is herein incorporated by reference), electroporation (JP S60-251887 A, which is herein incorporated by reference), and methods using particle guns (gene guns) (JP 2606856 B, JP 2517813 B, each of which is herein incorporated by reference). Among these, it is preferred to use a method using *Agrobacterium* (*Agrobacterium* method) to introduce the vector of the second disclosure into a plant to produce a transgenic plant (transgenic plant cells).

Furthermore, the vector of the second disclosure may also be introduced into, for example, an organism (e.g., a microorganism, yeast, animal cell, or insect cell) or a part thereof, an organ, a tissue, a cultured cell, a spheroplast, or a protoplast by any of the above or other DNA introduction methods to produce a cis-isoprenoid or polyisoprenoid.

The transgenic plant (transgenic plant cells) can be produced by the above or other methods. Here, the term "transgenic plant" conceptually includes not only transgenic plant cells produced by the above methods, but also all of their progeny or clones and even progeny plants obtained by subculturing the foregoing. Once obtaining transgenic plant cells into which the vector of the second disclosure has been introduced, progeny or clones can be produced from the transgenic plant cells by sexual or asexual reproduction, tissue culture, cell culture, cell fusion, or other techniques. Moreover, the transgenic plant cells, or their progeny or clones may be used to obtain reproductive materials (e.g., seeds, fruits, cuttings, stem tubers, root tubers, shoots, adventitious buds, adventitious embryos, callus, protoplasts), which may then be used to produce the transgenic plant on a large scale.

Techniques to regenerate plants (transgenic plants) from transgenic plant cells are already known; for example, Doi et al. disclose techniques for eucalyptus (Japanese Patent Application No. H11-127025, which is herein incorporated by reference), Fujimura et al. disclose techniques for rice (Fujimura et al., (1995), Plant Tissue Culture Lett., vol. 2: p. 74-, which is herein incorporated by reference), Shillito et al. disclose techniques for corn (Shillito et al., (1989), Bio/Technology, vol. 7: p. 581-, which is herein incorporated by reference), Visser et al. disclose techniques for potato (Visser et al., (1989), Theor. Appl. Genet., vol. 78: p. 589-, which is herein incorporated by reference), and Akama et al. disclose techniques for *Arabidopsis thaliana* (Akama et al., (1992), Plant Cell Rep., vol. 12: p. 7-, which is herein incorporated by reference). A person skilled in the art can regenerate plants from the transgenic plant cells with reference to these documents.

Whether a target protein gene is expressed in a regenerated plant may be determined by well-known methods. For example, Western blot analysis may be used to assess the expression of a target protein.

Seeds can be obtained from the transgenic plant, for example, as follows: The transgenic plant is rooted in an appropriate medium and transplanted to water-containing soil in a pot. The plant is grown under proper cultivation conditions to finally produce seeds, which are then collected. Moreover, plants can be grown from seeds, for example, as follows: Seeds obtained from the transgenic plant as described above are sown in water-containing soil and grown under proper cultivation conditions into plants.

According to the second disclosure, by introducing the vector of the second disclosure into a plant, the gene coding for the mutant CPT family protein, which is involved in polyisoprenoid biosynthesis, in the vector will be expressed to enable the production of a higher molecular weight polyisoprenoid in the plant as compared to before the gene recombination. Specifically, a high molecular weight cis-polyisoprenoid or polyisoprenoid can be produced by culturing, for example, transgenic plant cells produced as described above, callus obtained from the transgenic plant cells, or cells redifferentiated from the callus in an appropriate medium, or by growing, for example, transgenic plants regenerated from the transgenic plant cells, or plants grown from seeds obtained from these transgenic plants under proper cultivation conditions.

(Method for Producing Rubber Product)

The method for producing a rubber product of the second disclosure includes: producing a polyisoprenoid using a transgenic plant produced by introducing the vector of the second disclosure into a plant; kneading the polyisoprenoid with an additive to obtain a kneaded mixture; forming a raw rubber product from the kneaded mixture; and vulcanizing the raw rubber product.

The rubber product is as described above for the first disclosure.

When the rubber product is a pneumatic tire, or in other words, when the method for producing a rubber product of the second disclosure is the method for producing a pneumatic tire of the second disclosure, the raw rubber product forming step corresponds to the step of building a green tire from the kneaded mixture, and the vulcanization step corresponds to the step of vulcanizing the green tire. Thus, the method for producing a pneumatic tire of the second disclosure includes: producing a polyisoprenoid using a transgenic plant produced by introducing the vector of the second disclosure into a plant; kneading the polyisoprenoid with an additive to obtain a kneaded mixture; building a green tire from the kneaded mixture; and vulcanizing the green tire.

<Kneading Step>

In the kneading step, the polyisoprenoid produced by the transgenic plant produced by introducing the vector of the second disclosure into a plant is kneaded with an additive to obtain a kneaded mixture.

The polyisoprenoid produced by the transgenic plant produced by introducing the vector of the second disclosure into a plant can be collected by harvesting latex from the transgenic plant, and subjecting the latex to the solidification step described below.

Here, the method for harvesting latex from the transgenic plant is not limited, and conventional methods may be used. For example, latex may be harvested by collecting the emulsion oozing out from the cuts in the trunk of the plant (tapping), or the emulsion oozing out from the cut roots or other parts of the transgenic plant, or by crushing the cut tissue followed by extraction with an organic solvent.

<Solidification Step>

The harvested latex is subjected to a solidification step. The solidification may be carried out by any method, such as by adding the latex to a solvent that does not dissolve polyisoprenoids, such as ethanol, methanol, or acetone, or by adding an acid to the latex. Rubber (a type of polyisoprenoid) can be recovered as solids from the latex by the solidification step. The obtained rubber may be dried if necessary before use.

Any additive may be used including additives used in the production of rubber products. For example, when the rubber product is a pneumatic tire, examples of the additive include rubber components other than the rubber obtained from the latex, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

The kneading in the kneading step may be carried out using a rubber kneading machine such as an open roll mill, a Banbury mixer, or an internal mixer.

<Raw Rubber Product Forming Step (Green Tire Building Step in the Case of Tire)>

The raw rubber product forming step is as described above for the first disclosure.

<Vulcanization Step>

The vulcanization step is as described above for the first disclosure.

EXAMPLES

The present disclosure is specifically described with reference to examples, but the present disclosure is not limited to the examples.

A summary of the examples and comparative examples will be described first.

Example 1: Assay on Rubber Particles Using AtCPT5-C-Terminal HRT1

Comparative Example 1: Assay on Rubber Particles Using AtCPT5

In Example 1 and Comparative Example 1, the chain lengths of the products produced with a C-terminal mutant and a normal type of CPT incapable of interacting with a NgBR family protein were compared. Here, AtCPT5 corresponds to a CPT family protein not found on rubber particles, and HRT1 corresponds to a CPT family protein found on rubber particles.

Example 2: Assay on Rubber Particles Using HbCPT5-C-Terminal HRT1

Comparative Example 2: Assay on Rubber Particles Using HbCPT5

In Example 2 and Comparative Example 2, the chain lengths of the products produced with a C-terminal mutant and a normal type of CPT capable of interacting with a NgBR family protein were compared. Here, HbCPT5 corresponds to a CPT family protein not found on rubber particles, and HRT1 corresponds to a CPT family protein found on rubber particles.

(Acquisition of Each Gene)

(1) HRT1 Gene

[Extraction of Total RNA from *Hevea* Latex]

Total RNA was extracted from the latex of *Hevea brasiliensis* by the hot phenol method. To 6 mL of the latex were added 6 mL of a 100 mM sodium acetate buffer and 1 mL of a 10% SDS solution, followed by addition of 12 mL of water-saturated phenol pre-heated at 65° C. The mixture was incubated for five minutes at 65° C., agitated in a vortex mixer, and centrifuged at 7000 rpm for 10 minutes at room temperature. After the centrifugation, the supernatant was transferred to a new tube, 12 mL of a phenol:chloroform (1:1) solution was added, and they were agitated by shaking for two minutes. After the agitation, the resulting mixture was centrifuged again at 7000 rpm for 10 minutes at room temperature. Then, the supernatant was transferred to a new tube, 12 mL of a chloroform:isoamyl alcohol (24:1) solution was added, and they were agitated by shaking for two minutes. After the agitation, the resulting mixture was centrifuged again at 7000 rpm for 10 minutes at room temperature. Then, the supernatant was transferred to a new tube, 1.2 mL of a 3M sodium acetate solution and 13 mL of isopropanol were added, and they were agitated in a vortex mixer. The resulting mixture was incubated for 30 minutes at −20° C. to precipitate total RNA. The incubated mixture was centrifuged at 15000 rpm for 10 minutes at 4° C., and the supernatant was removed to collect a precipitate of total RNA. The collected total RNA was washed twice with 70% ethanol and then dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara) in accordance with the manual.

[Acquisition of HRT1 Gene from cDNA]

The prepared 1st strand cDNA was used as a template to obtain a HRT1 gene. PCR was performed using a KOD-plus-Neo (Toyobo) in accordance with the manual. The PCR reaction involved 35 cycles with each cycle consisting of seconds at 98° C., 30 seconds at 58° C., and 1 minute at 68° C.

The HRT1 gene was obtained using the following primers.

```
Primer 1:
                                    (SEQ ID NO:15)
5'-tttggatccgatggaattatacaacggtgagagg-3'

Primer 2:
                                    (SEQ ID NO: 16)
5'-tttgcggccgcttattttaagtattccttatgtttctcc-3'
```

A HRT1 gene was prepared as described above. The gene was sequenced to identify the full-length nucleotide sequence and amino acid sequence.

[Acquisition of HRBP Gene from cDNA]

The following primers were used.

```
Primer 3:
                                    (SEQ ID NO: 17)
5'-tttctcgagatggatttgaaacctggagctg-3'

Primer 4:
                                    (SEQ ID NO: 18)
5'-tttctcgagtcatgtaccataattttgctgcac-3'
```

A HRBP gene was prepared as described above. The gene was sequenced to identify the full-length nucleotide sequence and amino acid sequence (SEQ ID NO:11 and SEQ ID NO:12).

[Acquisition of REF Gene from cDNA]

The following primers were used.

```
Primer 5:
                                    (SEQ ID NO: 19)
5'-tttctcgagatggctgaagacgaagac-3'

Primer 6:
                                    (SEQ ID NO: 20)
5'-tttggatcctcaattctctccataaaac-3'
```

A REF gene was prepared as described above. The gene was sequenced to identify the full-length nucleotide sequence and amino acid sequence (SEQ ID NO:13 and SEQ ID NO:14).

[Vector Construction]

The obtained DNA fragments were subjected to dA addition and then inserted into a pGEM-T Easy vector using a pGEM-T Easy Vector System (Promega) to prepare pGEM-HRT1, pGEM-HRBP, and pGEM-REF.

[Transformation of *Escherichia coli*]

*Escherichia coli* DH5α was transformed with the prepared vectors, and the transformant was cultured on LB agar medium containing ampicillin and X-gal. Then, *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection. It was confirmed by sequence analysis that there were no mutations in the nucleotide sequence of the gene inserted in the collected plasmid.

(2) HbCPT5 Gene

A HbCPT5 gene was acquired by PCR using a rubber tree genome as a template.

[Extraction of Genome DNA from *Hevea* Leaf]

A genome DNA was obtained from a *Hevea* leaf by a cetyltrimethylammonium bromide (CTAB) method.

[Acquisition of HRBP Gene from Genome DNA]

PCR was performed using a KOD-plus-Neo (Toyobo) in accordance with the manual. The PCR reaction involved 35 cycles with each cycle consisting of 10 seconds at 98° C., 30 seconds at 58° C., and 2 minutes at 68° C.

The HbCPT5 gene was obtained using the following primers.

```
Primer 7:
                                       (SEQ ID NO: 21)
5'-GTGCTGGAATTCATGGAAATATTTGAGGCTGG-3'

Primer 8:
                                       (SEQ ID NO: 22)
5'-AAGCTTGTCGACTTAATGGTGATGGTGATGATGACCGGTACGCAAC
TGCTTCTTTTTCTTC-3'
```

A HbCPT5 gene was prepared as described above. The gene was sequenced to identify the full-length nucleotide sequence and amino acid sequence.

[Vector Construction]

The obtained PCR fragment was subjected to dA addition and then inserted into a pGEM-T Easy vector using a pGEM-T Easy Vector System (Promega) to prepare pGEM-HbCPT5.

[Transformation of *Escherichia coli*]

*Escherichia coli* DH5c was transformed with the prepared vector, and the transformant was cultured on LB agar medium containing ampicillin and X-gal. Then, *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection. It was confirmed by sequence analysis that there were no mutations in the nucleotide sequence of the gene inserted in the collected plasmid.

(3) AtCPT5 Gene

A full-length cDNA of AtCPT5 (At5g58780) was offered by the RIKEN BioResource Research center (Resource No. RAFL06-16-E16) via the National Bio-Resource Project.

(Preparation of Mutant Gene)

[Preparation of Fragments]

To prepare mutant genes, PCR fragments were prepared by PCR using the following primers. PCR was performed using a KOD-plus-Neo (Toyobo) in accordance with the manual. The PCR reaction involved 35 cycles with each cycle consisting of 10 seconds at 98° C., 30 seconds at 58° C., and 1 minute at 68° C.

AtCPT5 without C-Terminus (1-834)

```
Primer 9:
                                       (SEQ ID NO: 23)
Fw 5'-ACATCACCAAGATATCATGTTGTCTATTCTCTCTTCTCTTTTA
TCT-3'

Primer 10:
                                       (SEQ ID NO: 24)
Rv 5'-GTCGAAGACCAATATCAGGCCAAAGG-3'
```

HbCPT5 without C-Terminus (1-1023)

```
Primer 11:
                                       (SEQ ID NO: 25)
Fw 5'-ACATCACCAAGATATCATGGAAATATTTGAGGCTGG-3'

Primer 12:
                                       (SEQ ID NO: 26)
Rv 5'-GAAGACCAATCTCCGGCCAC-3'
```

HRT1 C-Terminus (787-873) Alone for Fusion to AtCPT5

```
Primer 13:
                                       (SEQ ID NO: 27)
Fw 5'-CCTTTGGCCTGATATTGGTCTTCGAC-3'

Primer 14:
                                       (SEQ ID NO: 28)
Rv 5'-TACAGGTTTTCCTCGAGTTATTTTAAG-3'
```

HRT1 C-Terminus (787-873) Alone for Fusion to HbCPT5

```
Primer 15:
                                       (SEQ ID NO: 29)
Fw 5'-GTGGCCGGAGATTGGTCTTC-3'

Primer 16:
                                       (SEQ ID NO: 30)
Rv 5'-TACAGGTTTTCCTCGAGTTATTTTAAG-3'
```

Each PCR product was electrophoresed on a 2.0% agarose gel. Then, a band in a target size was recovered from the gel using a FastGene™ gel-PCR extraction kit (Nippon Genetics Co., Ltd.). Overlap extension PCR was performed using the obtained PCR products as templates to prepare a chimeric sequence. The PCR reaction involved 30 cycles with each cycle consisting of 2 minutes at 94° C., 10 seconds at 98° C., 30 seconds at 55° C., and 30 seconds at 68° C.

AtCPT5 without C-Terminus+HRT1 C-Terminus Alone

```
Primer 17:
                                       (SEQ ID NO: 31)
Fw 5'-ACATCACCAAGATATCATGTTGTCTATTCTCTCTTCTCTTTTA
TCT-3'
```

-continued

```
Primer 18:
                               (SEQ ID NO: 32)
Rv 5'-TGATTGGCCGAGGCGGCC TTATTTTAAG-3'
```

HbCPT5 without C-Terminus+HRT1 C-Terminus Alone

```
    Primer 19:
                               (SEQ ID NO: 33)
    Fw 5'-ACATCACCAAGATATCATGGAAATATTTGAGGCTGG-3'

Primer 20:
                               (SEQ ID NO: 34)
    Rv 5'-TGATTGGCCGAGGCGGCC TTATTTTAAG-3'
```

The resulting PCR product was recovered from a 0.8% agarose gel, followed by dA addition using a 10× A-attachment mix (TOYOBO) and ligation to a pGEM-T EASY vector (Promega). *Escherichia coli* DH5α was transformed with the vector, and the transformant was applied to LB agar medium [+50 μg/mL Amp, +20 μL of 5% (w/v) X-gal, +25 μL of 100 mM IPTG] and cultured at 37° C. overnight, followed by blue/white screening. Several white colonies were selected and cultured with shaking overnight at 37° C. in 4 mL of LB liquid medium [+50 μg/mL Amp]. After the culture, the plasmid was collected using a FastGene™ Plasmid mini kit (Nippon Genetics Co., Ltd.) and digested with EcoRI (NEB) for 20 minutes to confirm the insertion of the insert. It was confirmed by sequence analysis that there were no mutations introduced in the PCR-amplified sequence.

(Preparation of Mutant Expression Vector)

A pEU-E01-MCS-TEV-His-C1 cell-free expression vector was treated with the restriction enzymes EcoRV and KpnI and then purified by gel recovery. The SLiCE solution used in a SLiCE reaction was prepared as described below.

An amount of 0.3 to 0.4 g of cultured *Escherichia coli* DH5α was gently suspended in 1.2 mL of 50 mM Tris-HCl (pH 8.0) containing 3% Triton X-100 and then incubated at room temperature for 10 minutes. The incubated suspension was centrifuged at 20000×g for 2 minutes at 4° C., and the supernatant was collected. To the supernatant was added an equal amount of a 80% glycerol solution to prepare a SLiCE solution. The SLiCE solution was divided into aliquots and stored at −80° C. until used.

[PCR]

Full-Length AtCPT5

```
Primer 21:
                               (SEQ ID NO: 35)
Fw 5'-ACATCACCAAGATATCATGTTGTCTATTCTCTCTTCTCTTTTA
TCT-3'

Primer 22:
                               (SEQ ID NO: 36)
Rv 5'-TGATTGGCCGAGGCGGCCTCAAACCCGACAGCCAA-3'
```

Full-Length HbCPT5

```
Primer 23:
                               (SEQ ID NO: 37)
Fw 5'-ACATCACCAAGATATCATGGAAATATTTGAGGCTGG-3'

Primer 24:
                               (SEQ ID NO: 38)
Rv 5'-TGATTGGCCGAGGCGGCCTACAACTGCTTCTTTTTCTTC-3'
```

AtCPT5-C-Terminal HRT1

```
Primer 25:
                               (SEQ ID NO: 39)
Fw 5'-ACATCACCAAGATATCATGTTGTCTATTCTCTCTTCTCTTTTA
TCT-3'

Primer 26:
                               (SEQ ID NO: 40)
Rv 5'-TGATTGGCCGAGGCGGCCTTATTTTAAG-3'
```

HbCPT5-C-Terminal HRT1

```
    Primer 27:
                               (SEQ ID NO: 41)
    Fw 5'-ACATCACCAAGATATCATGGAAATATTTGAGGCTGG-3'

Primer 28:
                               (SEQ ID NO: 42)
    Rv 5'-TGATTGGCCGAGGCGGCCTTATTTTAAG-3'
```

Each obtained PCR fragment and the restriction enzyme-treated vector were mixed at a ratio of 1:1 to 3:1. To the mixture were added a 10× SLiCE buffer (500 μM Tris-HCl (pH 7.5), 100 mM MgCl$_2$, 10 mM ATP, 10 mM DTT) in a volume equal to one-tenth of the final volume of the reaction system and the SLiCE solution in a volume equal to one-tenth of the final volume of the reaction system, and they were reacted at 37° C. for 15 minutes. Thus, pEU-AtCPT5 (Comparative Example 1), pEU-AtCPT-C-terminal HRT1 (Example 1), pEU-HbCPT5 (Comparative Example 2), and pEU-HbCPT5-C-terminal HRT1 (Example 2) were prepared.

[Transformation of *Escherichia coli*]

*Escherichia coli* DH5α was transformed with each prepared vector, and the transformant was cultured on LB agar medium containing ampicillin and X-gal. Then, *Escherichia coli* cells carrying the introduced target gene were selected by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

(Preparation of HRBP or REF Expression Vector)

pGEM-HRBP was treated with the restriction enzyme Xho I and then inserted into a pEU-E01-MCS-TEV-His-C1 cell-free expression vector treated similarly with the restriction enzyme Xho I to prepare pEU-C1-HRBP.

Moreover, pGEM-REF was treated with the restriction enzymes Xho I and Bam HI and then inserted into a pEUE01-MCS-TEV-His-C1 cell-free expression vector treated similarly with the restriction enzymes Xho I and Bam HI to prepare pEU-C1-REF.

[Transformation of *Escherichia coli*]

*Escherichia coli* DH5α was transformed with each prepared vector, and the transformant was cultured on LB agar medium containing ampicillin and X-gal. Then, *Escherichia coli* cells carrying the introduced target gene were selected by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

(Enzyme Assay)

[Preparation of Rubber Particles]

Rubber particles were prepared from the latex of *Hevea brasiliensis* (*Hevea* latex) by five stages of centrifugation. To 900 mL of *Hevea* latex was added 100 mL of a 1 M Tris buffer (pH 7.5) containing 20 mM dithiothreitol (DTT) to prepare a latex solution. The latex solution was centrifuged in stages at the following different speeds: 1000×g, 2000×g, 8000×g, 20000×g, and 50000×g. Each centrifugation stage was carried out for 45 minutes at 4° C. To the rubber particle layer left after the centrifugation at 50000×g was added 3-[(3-cholamidopropyl)dimethylammonio]-propane-sulfonate (CHAPS) to a final concentration of 0.1 to 2.0× CMC (0.1 to 2.0 times the critical micelle concentration CMC) to wash the rubber particles. After the washing, the rubber particles were collected by ultracentrifugation (40000×g, 4° C., 45 minutes) and re-suspended in an equal amount of a 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector acquired as described above as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The following amounts of materials were added to a dialysis cup (MWCO 12000, Bio-Teck). A total amount of 60 µL of a reaction solution was prepared according to the protocol of the WEPRO7240H expression kit. To the reaction solution was added 1 to 2 mg of the rubber particles. Separately, 650 µL of SUB-AMIX was added to a No. 2 PP container (Maruemu container).

The dialysis cup was set in the No. 2 PP container, and a protein synthesis reaction was initiated at 26° C. The addition of the mRNA and the replacement of the external dialysis solution (SUB-AMIX) were performed twice after the initiation of the reaction. The reaction was carried out for 24 hours.

[Collection of Reacted Rubber Particles]

The solution in the dialysis cup was transferred to a new 1.5 µL tube, and the reacted rubber particles were collected by ultracentrifugation (40000×g, 4° C., 45 minutes) and re-suspended in an equal amount of a 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM MgCl$_2$, 15 µM dimethylallyl diphosphate (DMAPP), 100 µM 1-14C isopentenyl diphosphate ([1-14C]IPP, specific activity 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by $^{14}$C counting using a liquid scintillation counter. A higher radioactivity (dpm) indicates a higher production of the very long chain polyisoprenoid (rubber) and a higher rubber synthesis activity.

[Measurement of Molecular Weight Distribution of Synthesized Very Long Chain Polyisoprenoid]

Figure 2:
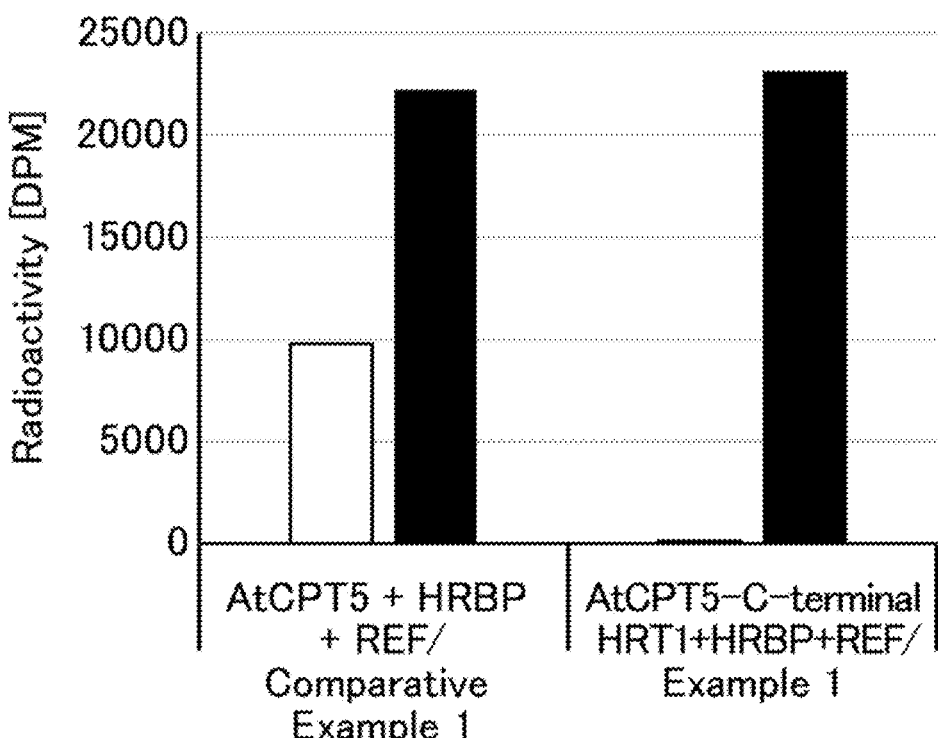
FIG. 2 is a graph that shows the measured enzymatic activities in Example 1 and Comparative Example 1.

The molecular weight distribution of the very long chain polyisoprenoid (rubber) synthesized as above was measured under the following conditions by radio-HPLC. FIG. 2 shows the results.

HPLC system: a product of GILSON

Column: TSK guard column MP(XL) available from Tosoh Corporation, TSKgel multipore H$_{XL}$-M (two columns)

Column temperature: 40° C.

Solvent: THF available from Merck

Flow rate: 1 mL/min

UV detection: 215 nm

RI detection: Ramona Star (Raytest GmbH)

(Test Results)

Comparative Example 1 and Example 1

Figure 3:
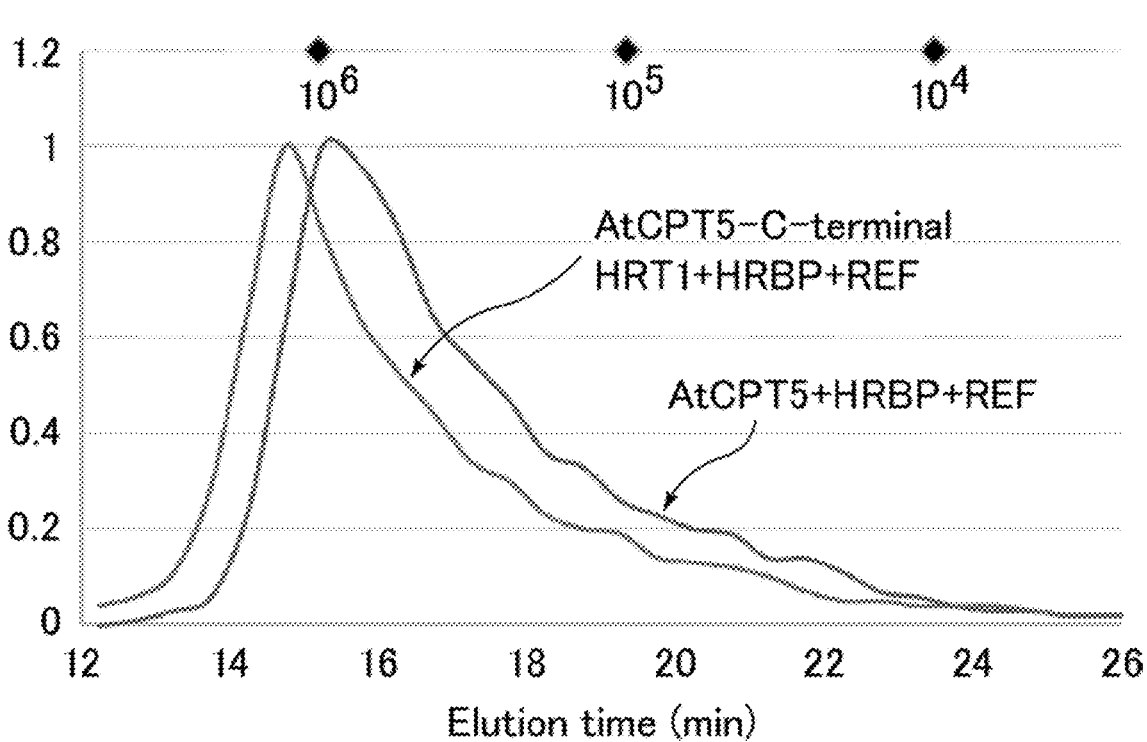
FIG. 3 is a graph that shows the measured molecular weight distributions of the polyisoprenoids synthesized in Example 1 and Comparative Example 1.

FIG. 2 and FIG. 3 show the results. As shown by FIG. 2 and FIG. 3, the short- or medium-chain isoprene chain synthesis activity was high in Comparative Example 1, while, in Example 1, the short- or medium-chain isoprene chain synthesis was decreased to about 0.01 times that of Comparative Example 1. Although the long-chain isoprene chain synthesis activity apparently seems to be the same, an increase in the molecular weight of the product of Example 1 was demonstrated by a molecular weight distribution analysis by GPC.

Comparative Example 2 and Example 2

Figure 4:
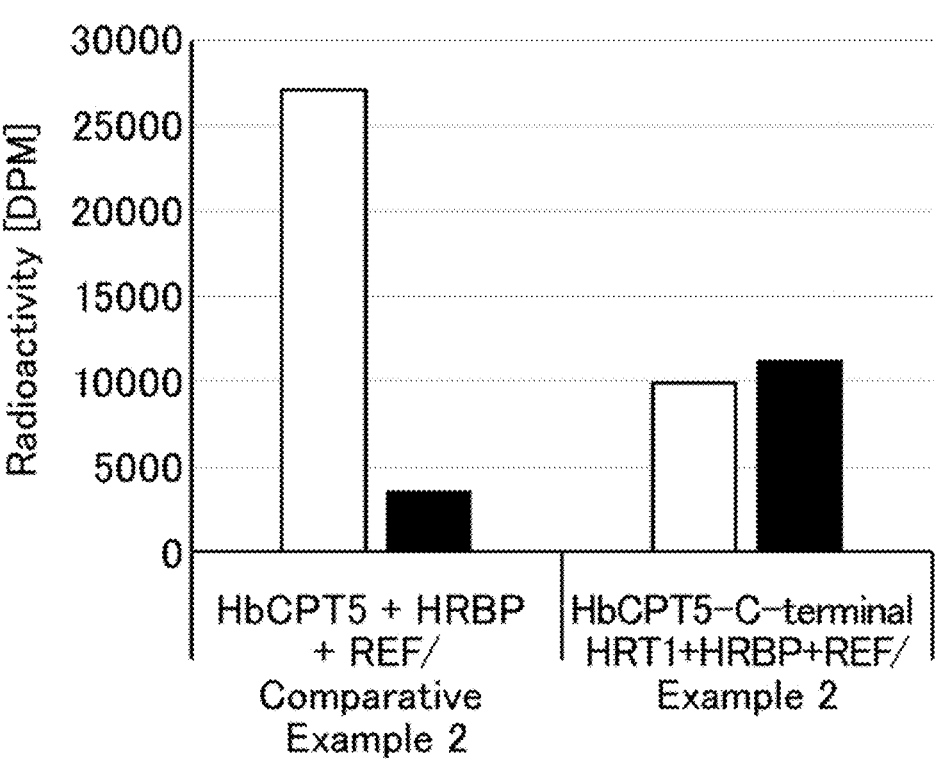
FIG. 4 is a graph that shows the measured enzymatic activities in Example 2 and Comparative Example 2.

FIG. 4 shows the results. As shown by FIG. 4, the short- or medium-chain isoprene chain synthesis activity was high in Comparative Example 2, while, in Example 2, the short- or medium-chain isoprene chain synthesis was decreased to about 0.37 times that of Comparative Example 2, but instead the long-chain isoprene chain synthesis activity was increased to about 3.1 times. This reveals that the use of HbCPT5 in which the C-terminus was replaced with that of HRT1 increases the molecular weight of the product chain.

The experimental results demonstrate the following: a mutant cis-prenyltransferase (CPT) family protein obtained by mutating the amino acid sequence of a C-terminal region of a cis-prenyltransferase (CPT) family protein not found on rubber particles to be identical or similar to the amino acid sequence of a C-terminal region of a cis-prenyltransferase (CPT) family protein found on rubber particles enables the production of a higher molecular weight polyisoprenoid than that produced with the unmutated cis-prenyltransferase (CPT) family protein. Then, a method for producing a polyisoprenoid using the mutant cis-prenyltransferase (CPT) family protein enables the production of a higher molecular weight polyisoprenoid than that produced with the unmutated cis-prenyltransferase (CPT) family protein.

Thus, it is also demonstrated that when a vector that contains a gene coding for the mutant cis-prenyltransferase (CPT) family protein of the first disclosure is introduced into a plant, the gene coding for the mutant cis-prenyltransferase (CPT) family protein of the first disclosure in the vector will be expressed to enable the production of a higher molecular weight polyisoprenoid in the plant as compared to before the gene recombination.

Exemplary embodiments of the present disclosure include:

Embodiment 1. A mutant cis-prenyltransferase (CPT) family protein, obtained by mutating an amino acid sequence of a C-terminal region of a cis-prenyltransferase (CPT) family protein not found on rubber particles to be identical or similar to an amino acid sequence of a C-terminal region of a cis-prenyltransferase (CPT) family protein found on rubber particles.

Embodiment 2. The mutant cis-prenyltransferase (CPT) family protein according to Embodiment 1, wherein the amino acid sequence of the C-terminal region of the cis-prenyltransferase (CPT) family protein not found on rubber particles is substituted by an amino acid sequence that is identical or similar to the amino acid sequence of the C-terminal region of the cis-prenyltransferase (CPT) family protein found on rubber particles.

Embodiment 3. The mutant cis-prenyltransferase (CPT) family protein according to Embodiment 1 or 2, wherein the cis-prenyltransferase (CPT) family protein found on rubber particles is a cis-prenyltransferase (CPT) family protein found on rubber particles derived from a plant of the genus *Hevea* or *Taraxacum*.

Embodiment 4. The mutant cis-prenyltransferase (CPT) family protein according to Embodiment 1 or 2, wherein the cis-prenyltransferase (CPT) family protein found on rubber particles is a cis-prenyltransferase (CPT) family protein found on rubber particles derived from *Hevea brasiliensis* or *Taraxacum kok-saghyz*.

Embodiment 5. The mutant cis-prenyltransferase (CPT) family protein according to any one of Embodiments 1 to 4, wherein the amino acid sequence of the C-terminal region of the cis-prenyltransferase (CPT) family protein not found on rubber particles is a C-terminus-containing amino acid sequence within 50 amino acids upstream of a C-terminus of the protein.

Embodiment 6. A method for producing a polyisoprenoid, the method including using the mutant cis-prenyltransferase (CPT) family protein according to any one of Embodiments 1 to 5.

Embodiment 7. The method for producing a polyisoprenoid according to Embodiment 6, wherein the method includes binding the mutant cis-prenyltransferase (CPT) family protein according to any one of Embodiments 1 to 5 to membrane particles in vitro.

Embodiment 8. A method for producing a pneumatic tire, the method including:

producing a polyisoprenoid by the method for producing a polyisoprenoid according to Embodiment 6 or 7;

kneading the polyisoprenoid with an additive to obtain a kneaded mixture;

building a green tire from the kneaded mixture; and vulcanizing the green tire.

Embodiment 9. A method for producing a rubber product, the method including:

producing a polyisoprenoid by the method for producing a polyisoprenoid according to Embodiment 6 or 7;

kneading the polyisoprenoid with an additive to obtain a kneaded mixture;

forming a raw rubber product from the kneaded mixture; and vulcanizing the raw rubber product.

Embodiment 10. A vector, containing a gene coding for the mutant cis-prenyltransferase (CPT) family protein according to any one of Embodiments 1 to 5.

Embodiment 11. The vector according to Embodiment 10, containing:

a promoter for use in protein expression in a plant; and the gene coding for the mutant cis-prenyltransferase (CPT) family protein, functionally linked to the promoter.

Embodiment 12. The vector according to Embodiment 10, containing:

a promoter having a promoter activity that drives laticifer-specific gene expression; and the gene coding for the mutant cis-prenyltransferase (CPT) family protein, functionally linked to the promoter.

Embodiment 13. A transgenic plant into which the vector according to any one of Embodiments 10 to 12 has been introduced.

Embodiment 14. A method for producing a polyisoprenoid in a plant by introducing the vector according to any one of Embodiments 10 to 12 into the plant.

Embodiment 15. A method for producing a pneumatic tire, the method including:

producing a polyisoprenoid using a transgenic plant produced by introducing the vector according to any one of Embodiments 10 to 12 into a plant;

kneading the polyisoprenoid with an additive to obtain a kneaded mixture;

building a green tire from the kneaded mixture; and vulcanizing the green tire.

Embodiment 16. A method for producing a rubber product, the method including:

producing a polyisoprenoid using a transgenic plant produced by introducing the vector according to any one of Embodiments 10 to 12 into a plant;

kneading the polyisoprenoid with an additive to obtain a kneaded mixture;

forming a raw rubber product from the kneaded mixture; and vulcanizing the raw rubber product.

---

The invention claimed is:

1. A method for producing a polyisoprenoid, the method comprising binding a cis-prenyltransferase comprising at least 95% sequence identity to the polypeptide of SEQ ID NO: 7 or 8 to a Nogo-B receptor (NgBR) in vitro, wherein the NgBR receptor is integrated in a membrane of a rubber particle, thereby producing said polyisoprenoid, wherein the cys-prenyltransferase catalyzes a cis-chain elongation reaction of an isoprenoid compound.

2. A method for producing a pneumatic tire, the method comprising:

producing a polyisoprenoid by binding a cis-prenyltransferase comprising at least 95% sequence identity to the polypeptide of SEQ ID NO: 7 or 8 to a Nogo-B receptor (NgBR) in vitro, wherein the NgBR receptor is integrated in a membrane of a rubber particle, thereby producing said polyisoprenoid, and wherein the cys-prenyltransferase catalyzes a cis-chain elongation reaction of an isoprenoid compound;

kneading the polyisoprenoid with an additive to obtain a kneaded mixture;

building a green tire from the kneaded mixture; and vulcanizing the green tire.

3. A method for producing a rubber product, the method comprising:

producing a polyisoprenoid by binding a cis-prenyltransferase comprising at least 95% sequence identity to the polypeptide of SEQ ID NO: 7 or 8 to a Nogo-B receptor (NgBR) in vitro, wherein the NgBR receptor is integrated in a membrane of a rubber particle, thereby producing said polyisoprenoid, and wherein the cys-prenyltransferase catalyzes a cis-chain elongation reaction of an isoprenoid compound;

kneading the polyisoprenoid with an additive to obtain a kneaded mixture;

forming a raw rubber product from the kneaded mixture; and vulcanizing the raw rubber product.

4. The method for producing a polyisoprenoid according to claim 1, wherein the cis-prenyltransferase comprises at least 95% sequence identity to the polypeptide of SEQ ID NO: 7.

5. The method for producing a polyisoprenoid according to claim 4, wherein the cis-prenyltransferase comprises at least 98% sequence identity to the polypeptide of SEQ ID NO: 7.

6. The method for producing a polyisoprenoid according to claim 1, wherein the cis-prenyltransferase comprises at least 95% sequence identity to the polypeptide of SEQ ID NO: 8.

7. The method for producing a polyisoprenoid according to claim 6, wherein the cis-prenyltransferase comprises at least 98% sequence identity to the polypeptide of SEQ ID NO: 8.

* * * * *